United States Patent

Zagar et al.

[11] Patent Number: 6,054,412
[45] Date of Patent: Apr. 25, 2000

[54] SUBSTITUTED 4,5-DI(TRIFLUOROMETHYL) PYRAZOLES AND THEIR USE AS HERBICIDES AND FOR DESICCATING/ DEFOLIATING PLANTS

[75] Inventors: Cyrill Zagar, Ludwigshafen; Gerhard Hamprecht, Weinheim; Elisabeth Heistracher, Mannheim; Olaf Menke, Altleiningen; Peter Schäfer, Ottersheim; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/043,113
[22] PCT Filed: Oct. 22, 1996
[86] PCT No.: PCT/EP96/04580
   § 371 Date: Apr. 21, 1998
   § 102(e) Date: Apr. 21, 1998
[87] PCT Pub. No.: WO97/15509
   PCT Pub. Date: May 1, 1997

[30] Foreign Application Priority Data

Oct. 26, 1995 [DE] Germany .............. 195 39 835

[51] Int. Cl.[7] .......................... A01N 43/56; C07D 231/12
[52] U.S. Cl. ........................................ 504/169; 548/377.1
[58] Field of Search ..................... 548/377.1; 504/169

[56] References Cited

U.S. PATENT DOCUMENTS 5,672,715 9/1997 Hamper et al. ............... 548/374.1

OTHER PUBLICATIONS

Hartmann et al., Diazo Compounds and Azides, Phosporus 5(1), 21–29, Dec. 1974.

*Primary Examiner*—Johann Richter
*Assistant Examiner*—Dominic Keating
*Attorney, Agent, or Firm*—Keil & Weinkauf

[57] ABSTRACT

Substituted 4,5-di(trifluoromethyl)pyrazoles I

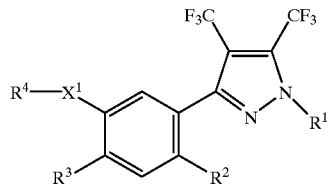

and salts thereof,

Use: as herbicides; for the desiccation/defoliation of plants.

10 Claims, No Drawings

SUBSTITUTED 4,5-DI(TRIFLUOROMETHYL) PYRAZOLES AND THEIR USE AS HERBICIDES AND FOR DESICCATING/DEFOLIATING PLANTS

This application is a 371 of PCT/EP96/04580 filed Oct. 22, 1996.

The present invention relates to novel substituted 4,5-di(trifluoromethyl)pyrazoles of the formula I

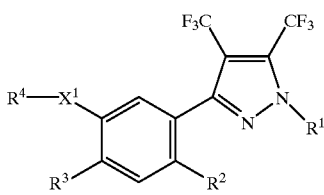

where the variables have the following meanings:
$R^1$ is $C_1$–$C_4$-alkyl or $C_1$–$C_4$-haloalkyl;
$R^2$ is hydrogen or halogen;
$R^3$ is cyano, halogen, $C_1$–$C_4$-alkyl or $C_1$–$C_4$-haloalkyl;
$R^4$ is hydrogen, nitro, cyano, halogen, —O—$X^2$—$R^5$ —O—CO—$X^2$—$R^5$, —N($X^2$—$R^5$) ($X^3$—$R^6$), —N($X^2$—$R^5$)—$SO_2$—$X^3$—$R^6$, —N($SO_2$—$X^2$—$R^5$)($SO_2$—$X^3$—$R^6$), —N($X^2$—$R^5$)(CO—$X^3$—$R^6$), —N($X^2$—$R^5$)(O—$X^3$—$R^6$), —S—$X^2$—$R^5$—SO—$X^2$—$R^5$, —$SO_2$—$X^2$—$R^5$, —$SO_2$—O—$X^2$—$R^5$, —$SO_2$—N($X^2$—$R^5$) ($X^3$—$R^6$), —CO—$X^2$—$R^5$, —C(=NOR$^7$)—$X^2$—$R^5$, —CO—O—$X^2$—$R^5$, —CO—S—$X^2$—$R^5$, —CO—N($X^2$—$R^5$)($X^3$—$R^6$), or —CO—N($X^2$—$R^5$)(O—$X^3$—$R^6$);

$X^1$, $X^2$ and $X^3$ independently of one another are a chemical bond or an ethene-1,2-diyl, methylene, ethylene or propane-1,3-diyl chain, each of which can be unsubstituted or have attached to it one or two of the following substituents: halogen, cyano, carboxyl, $C_1$–$C_4$-alkyl, $C_1$–$C_4$-haloalkyl, ($C_1$–$C_4$-alkoxy)carbonyl, $C_1$–$C_4$-alkoxy, di-($C_1$–$C_4$-alkyl)amino, $C_1$–$C_6$-haloalkyl and/or phenyl, which, in turn, can have attached to it, if desired, one to three halogen atoms, nitro, carboxyl, $C_1$–$C_4$-alkyl, $C_1$–$C_4$-haloalkyl and/or ($C_1$–$C_4$-alkoxy)carbonyl groups, it furthermore being possible for the methylene, ethylene or propane-1,3-diyl chain to have attached to it a hydroxyl, amino or $C_1$–$C_4$-alkylamino radical;

$R^5$ and $R^6$ independently of one another are —Z—$R^8$, hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl which can contain a carbonyl or thiocarbonyl ring member, phenyl or 3- to 7-membered heterocyclyl which can contain a carbonyl or thiocarbonyl ring member, it being possible for the cycloalkyl rings, the phenyl ring and the heterocyclyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl)carbonyloxy and di-($C_1$–$C_4$-alkyl)amino;

$R^7$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl-$C_1$–$C_4$-alkyl;

Z is methylene which can be unsubstituted or have attached to it one or two substituents, in each case selected from the group consisting of $C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_4$-alkoxy)carbonyl-$C_1$–$C_4$-alkyl and phenyl-$C_1$–$C_4$-alkyl, it being possible for the phenyl ring to be unsubstituted or to have attached to it, in turn, one to three radicals, in each case selected from the group consisting of halogen, cyano, nitro, carboxyl, $C_1$–$C_4$-alkyl, $C_1$–$C_4$-haloalkyl and ($C_1$–$C_4$-alkoxy)carbonyl;

$R^8$ is hydrogen, nitro, cyano, halogen, —OR$^9$, —N(R$^{10}$)R$^{10}$, —N(R$^9$)—OR$^{10}$, —SR$^9$, —SO—R$^9$, —$SO_2$—R$^9$, —$SO_2$—OR$^9$, —$SO_2$—N(R$^9$)R$^{10}$, —CO—R$^9$, —C(=NOR$^{11}$)—R$^9$, —CO—OR$^9$, —CO—SR$^9$, —CO—N(R$^9$)R$^{10}$ or —CO—N(R$^9$)—OR$^{10}$—;

$R^9$ and $R^{10}$ independently of one another are hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–Ce-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, it being possible for the cycloalkyl and heterocyclyl rings to contain in each case one carbonyl or thiocarbonyl ring member and it being possible for the cycloalkyl, phenyl and heterocyclyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl)carbonyloxy and di-($C_1$–$C_4$-alkyl)amino;

$R^{11}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl-$C_1$–$C_4$-alkyl;

and to the agriculturally useful salts of the compounds I.

Moreover, the invention relates to the use of the compounds I as herbicides and/or for the desiccation and/or defoliation of plants, herbicidal compositions and compositions for the desiccation and/or defoliation of plants which comprise the compounds I as active ingredients, processes for the preparation of the compounds I and of herbicidal compositions and compositions for the desiccation and/or defoliation of plants using the compounds I, and methods of controlling undesirable vegetation and for the desiccation and/or defoliation of plants using the compounds I.

JP-A 02/300 173 describes herbicidally active phenylpyrazoles of the formula IIa

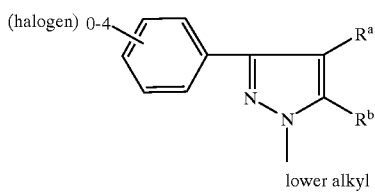

where
- $R^a$ is hydrogen, cyano, halogen, lower alkyl or lower alkoxycarbonyl and
- $R^b$ is, inter alia, hydrogen, cyano, halogen or unsubstituted or halogen-substituted lower alkyl.

Some of the compounds of the formula I where $R^1=C_1-C_4$-alkyl and where either
- $R^2$ is chlorine, bromine or iodine, $R^3$ is $C_1-C_4$-alkyl or $C_3-C_4$-haloalkyl and $X^1-R^4$ is hydrogen, or
- $R^2$ is hydrogen, $R^3$ is chlorine, bromine or iodine and $R^4$ is hydrogen, halogen, cyano, hydroxyl, —O—CO—CH$_3$, formyl, —CH=NOR$^7$, —CO—O—X$^2$—R$^5$, —CO—N(X$^2$—R$^5$) (X$^3$—R$^6$) or —CO—N(X$^2$—R$^5$) (O—X$^3$—R$^6$), or
- $R^2$ is hydrogen, $R^3$ is cyano and $R^4$ is chlorine, bromine, iodine, methoxy, difluoromethoxy, trifluoromethoxy or nitro, are a selection from the very broad range of herbicidally active and plant-growth-regulating compounds of WO 94/05153.

Moreover, some of the 4,5-di(trifluoromethyl)pyrazoles I where
$R^2$=halogen formally come under the general formula of the 3-phenylpyrazoles taught as herbicides in WO 96/15115, which has an earlier priority date.

Moreover, JP-A 03/163 063 describes 3-phenylpyrazole derivatives of the formula III

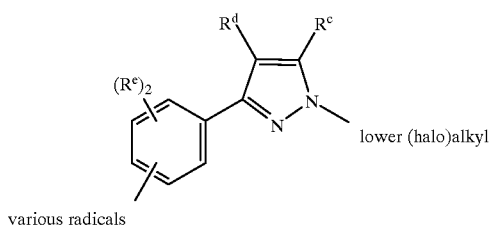

where $R^c$ and $R^d$ are, inter alia, lower haloalkyl and each $R^e$ is, inter alia, halogen or lower (halo)alkyl as herbicides. Individual compounds where $R^c$ and/or $R^d$=haloalkyl, however, cannot be found in this publication. In the subsequent application EP-A-0 361 114, $R^c$ was finally limited to hydroxyl, mercapto, lower(halo)alkoxy or lower(halo)alkyltio and $R^d$ was finally limited to hydrogen or halogen.

EP-A-0 289 919, EP-A 353 571 and EP-A-0 353 674 relate to certain insecticides, acaricides and nematicides, which are prepared using, inter alia, also, with suitable selection of substituents, some pyrazoles of the type of the compounds I as suitable precursors.

Other pyrazole intermediates whose general formula formally also covers 3-phenylpyrazoles of the type of the compounds I when suitable substituents are chosen are mentioned
- in JP 01/190 670 and in JP 63/112 566 for the preparation of 4(3H)-pyrimidinone derivatives which are said to have an insecticidal, acaricidal, nematicidal and fungicidal action;
- in EP-A-0 310 386 for the preparation of 4-Aryl-5-carbamoyl-1,4-dihydropyridines, which are said to act as antagonists to certain pharmaceuticals;
- in DE-A 195 00 439, which has an earlier priority date, for the preparation of thiocarboxamides which are taught as herbicides.

Finally, WO 95/06036 describes a process for the preparation of pyrazole and its derivatives. The very general definitions of radicals formally also include 3-phenylpyrazoles of the type of the compounds I.

Since the herbicidal properties of the hitherto known herbicidally active 3-phenylpyrazoles are not always entirely satisfactory with a view to the harmful plants, it was an object of the present invention to provide novel 3-phenylpyrazoles with which better tailored control of undesirable plants can be effected than was hitherto possible. The object also extended to providing novel compounds which have a desiccant/defoliant action.

We have found that this object is achieved by the present substituted 4,5-di(trifluoromethyl)pyrazoles of the formula I.

Furthermore, we have found herbicidal compositions which comprise the compounds I and have a very good herbicidal action. Moreover, we have found processes for the preparation of these compositions and methods of controlling undesirable vegetation using the compounds I.

Furthermore, we have found that the compounds I are also suitable for the desiccation/defoliation of parts of plants, suitable plants being crop plants such as cotton, potatoes, oilseed rape, sunflowers, soybeans or field beans, in particular cotton. Correspondingly, we have found compositions for the desiccation and/or defoliation of plants, processes for the preparation of these compositions and methods for the desiccation and/or defoliation of plants using the compounds I.

Depending on the substitution pattern, the compounds of the formula I can contain one or more chiral centers, in which case they are present in the form of enantiomer or diastereomer mixtures. The invention relates both to the pure enantiomers or diastereomers and to mixtures of these.

The organic moieties mentioned in the definition of the substituents $R^1$, $R^3$, $R^5$, $R^6$, $R^7$ and $R^9$ to $R^{11}$ or as radicals on cycloalkyl, phenyl or heterocyclic rings or on $X^1$ to $X^3$ and Z—and the meaning of halogen—are collective terms for individual enumerations of each of the group members. All carbon chains, ie. all alkyl, haloalkyl, alkenyl, haloalkenyl and alkynyl moieties, can be straight-chain or branched. Halogenated substituents preferably have attached to them one to five identical or different halogen atoms. The meaning of halogen is in each case fluorine, chlorine, bromine or iodine.

Other meanings are as follows:

$C_1-C_4$-alkyl and the alkyl moieties of $(C_1-C_4$-alkyl)carbonyl and $(C_1-C_4$-alkyl)carbonyloxy are: methyl, ethyl, n-propyl, 1-methylethyl, n-butyl, 1-methylpropyl, 2-methylpropyl and 1,1-dimethylethyl;

$C_1-C_4$-haloalkyl and the haloalkyl moieties of $(C_1-C_4$-haloalkyl)carbonyl and $(C_1-C_4$-haloalkyl)carbonyloxy are: a $C_1-C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2- fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-alkyl is: $C_1$–$C_4$-alkyl as mentioned above and, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethyl-butyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$–$C_6$-haloalkyl is: a $C_1$–$C_6$-alkyl radical as mentioned above which is partially or fully substituted by fluorine, chlorine, bromine and/or iodine, eg. one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

phenyl-$C_1$–$C_4$-alkyl is: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)-eth-1-yl or 1-(phenylmethyl)prop-1-yl, preferably benzyl or 2-phenylethyl;

heterocyclyl-$C_1$–$C_4$-alkyl is: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 3-heterocyclylbut-2-yl, 4-heterocyclylbut-2-yl, 1-(heterocyclylmethyl)eth-1-yl, 1-(heterocyclylmethyl)-1-(methyl)eth-1-yl or 1-(heterocyclylmethyl)prop-1-yl, preferably heterocyclylmethyl or 2-heterocyclylethyl;

$C_1$–$C_4$-alkoxy is: methoxy, ethoxy, n-propoxy, 1-methylethoxy, n-butoxy, 1-methylpropoxy, 2-methylpropoxy or 1,1-dimethylethoxy, preferably methoxy, ethoxy or 1-methylethoxy;

$C_1$–$C_4$-haloalkoxy is: a $C_1$–$C_4$-alkoxy radical as mentioned above which is partially or fully substituted by fluorine, chlorine, bromine and/or iodine, eg. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluorethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, preferably difluoromethoxy, trifluoromethoxy, dichlorofluoromethoxy, chlorodifluoromethoxy or 2,2,2-trifluoroethoxy;

$C_1$–$C_6$-alkylthio is: methylthio, ethylthio, n-propylthio, 1-methylethylthio, n-butylthio, 1-methylpropylthio, 2-methylpropylthio or 1,1-dimethylethylthio, preferably methylthio or ethylthio;

$C_1$–$C_4$-alkoxy-$C_1$–$C_4$-alkyl is: $C_1$–$C_4$-alkyl which is substituted by $C_1$–$C_4$-alkoxy as mentioned above, eg. methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy) ethyl, 2-( n-propoxy) ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy) propyl, 2-(n-propoxy)propyl, 2-(1-methylethoxy)-propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy) propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy) butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)-butyl, 3-(n-propoxy)butyl, 3-(1-methylethoxy)butyl, 3-(n-butoxy)butyl, 3-(1-methylpropoxy)butyl, 3-(2-methylpropoxy)-butyl, 3-(1,1-dimethylethoxy)butyl, 4-(methoxy)butyl, 4-(ethoxy) butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl or 2-ethoxyethyl;

$C_1$–$C_4$-alkylthio-$C_1$–$C_4$-alkyl is: $C_1$–$C_4$-alkyl which is substituted by $C_1$–$C_4$-alkylthio as mentioned above, eq. methylthiomethyl, ethylthiomethyl, n-propylthiomethyl, (1-methylethylthio)methyl, n-butylthiomethyl, (1-methylpropylthio)methyl, (2-methylpropylthio) methyl, (1,1-dimethylethylthio)methyl, 2-(methylthio) ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)-butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably methylthiomethyl, ethylthiomethyl, 2-methylthioethyl or 2-ethylthioethyl; ($C_1$–$C_4$-alkoxy)carbonyl is: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, preferably methoxycarbonyl or ethoxycarbonyl; ($C_1$–$C_4$-alkoxy)carbonyl-$C_1$–$C_4$-alkyl is: $C_1$–$C_4$-alkyl which is substituted by ($C_1$–$C_4$-alkoxy)carbonyl as mentioned above, eq. methoxycarbonylmethyl, ethoxycarbonylmethyl, n-propoxycarbonylmethyl, (1-methylethoxycarbonyl)methyl, n-butoxycarbonylmethyl, (1-methylpropoxycarbonyl)methyl, (2-methylpropoxycarbonyl)methyl, (1,1-dimethylethoxycarbonyl)methyl, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)-propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)-propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)-butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably methoxycarbonylmethyl, ethoxycarbonylmethyl, 1-(methoxycarbonyl)ethyl or 1-(ethoxycarbonyl)ethyl;

$C_1$–$C_4$-alkylsulfonyl is: methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl, preferably methylsulfonyl or ethylsulfonyl; $C_1$–$C_4$-haloalkylsulfonyl is: a $C_1$–$C_4$-alkylsulfonyl radical—as mentioned above—which is partially or fully substituted by fluorine, chlorine, bromine and/or iodine, eg. chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichloro-fluoromethylsulfonyl, chlorodifluoromethylsulfonyl, 2-fluoroethylsulfonyl, 2-chloroethylsulfonyl, 2-bromo- ethylsulfonyl, 2-iodoethylsulfonyl, 2,2-difluoroethyl- sulfonyl, 2,2,2-trifluoroethylsulfonyl, 2-chloro-2-fluoro-ethylsulfonyl, 2-chloro-2,2-difluoroethylsulfonyl, 2, 2-di-chloro-2-fluoroethylsulfonyl, 2,2,2-trichloro-ethylsulfonyl, pentafluoroethylsulfonyl, 2-fluoropropyl-sulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, 2,2,3,3,3-pentafluoropropylsulfonyl, heptafluoro-propylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutyl-sulfonyl, 4-bromobutylsulfonyl or nonafluorobutylsulfonyl, preferably chloromethylsulfonyl, trifluoromethylsulfonyl or 2,2,2-trifluoroethylsulfonyl;

$C_1$–$C_4$-alkylamino is: methylamino, ethylamino, n-propylamino, 1-methylethylamino, n-butylamino, 1-methylpropylamino, 2-methylpropylamino and 1,1-dimethylethylamino, preferably methylamino and ethylamino;

di-($C_1$–$C_4$-alkyl)amino is: N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)-amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1, 1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N,N-dimethylamino or N,N-diethylamino;

$C_2$–$C_6$-alkenyl is: vinyl, prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-haloalkenyl is: $C_2$–$C_6$-alkenyl as mentioned above which is partially or fully substituted by fluorine, chlorine and/or bromine, eg. 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl, preferably $C_3$- or $C_4$-haloalkenyl;

$C_2$–$C_6$-alkynyl is: ethynyl and $C_3$–$C_6$-alkynyl such as prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_2$–$C_6$-haloalkynyl is: $C_2$–$C_6$-alkynyl as mentioned above which is partially or fully substituted by fluorine, chlorine and/or bromine, eg. 1,1-difluoroprop-2-yn-1-yl, 1,1-difluorobut-2-yn-1-yl, 4-fluorobut-2-yn-1-yl, 4-chlorobut-2-yn-1-yl, 5-fluoropent-3-yn-1-yl or 6-fluorohex-4-yn-1-yl, preferably $C_3$- or $C_4$-haloalkynyl;

$C_3$–$C_8$-cycloalkyl is: cyclopropyl, cyclobutyl, cyclopentyl, cyclohexyl, cycloheptyl or cyclooctyl;

$C_3$–$C_8$-cycloalkyl which contains a carbonyl or thiocarbonyl ring member is, for example, cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_3$–$C_8$-cycloalkyl-$C_1$–$C_4$-alkyl is: cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl 1-cyclopropylbut-2-yl, 2-cyclopropylbut-2-yl, 3-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-(methyl)eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexyl-but-1-yl, 4-cyclohexylbut-1-yl, 1-cyclohexylbut-2-yl, 2-cyclohexylbut-2-yl, 3-cyclohexylbut-2-yl, 3-cyclohexylbut-2-yl, 4-cyclohexylbut-2-yl, 1-(cyclohexylmethyl)eth-1-yl, 1-(cyclohexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 4-cycloheptylbut-2-yl, 1-(cycloheptylmethyl)eth-1-yl, 1-(cycloheptylmethyl)-1-(methyl)eth-1-yl, 1-(cycloheptylmethyl)-prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-(methyl)eth-1-yl or 1-(cyclooctylmethyl)prop-1-yl, preferably cyclopropylmethyl, cyclobutylmethyl, cyclopentylmethyl or cyclohexylmethyl;

$C_3$–$C_8$-cycloalkyl-$C_1$–$C_4$-alkyl which contains a carbonyl or thiocarbonyl ring member, is, for example, cyclobutanon-2-ylmethyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl) ethyl, 1-( cyclobutanon-3-yl) ethyl, 1-(cyclopentanon-2-yl)ethyl, 1-(cyclopentanon-3-yl) ethyl, 1-(cyclohexanon-2-yl)ethyl, 1-(cyclohexanon-4-yl) ethyl, 1-(cycloheptanon-2-yl)ethyl, 1-(cyclooctanon-2-yl) ethyl, 1-(cyclobutanethion-n-2-yl)ethyl, 1-(cyclobutanethion-3-yl)ethyl, 1-(cyclopentanethion-2-yl)-ethyl, 1- ( cyclopentanethion-3-yl ) ethyl, 1-(cyclohexanethion-2-yl)ethyl, 1-(cyclohexanethion-4-yl)ethyl, 1-(cycloheptanethion-2-yl)ethyl, 1-(cyclooctanethion-2-yl)ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl)ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)-ethyl, 2-(cyclopentanethion-2-yl)ethyl, 2-(cyclopentanethion-3-yl)ethyl, 2-(cyclohexanethion-2-yl)ethyl, 2-(cyclohexanethion-4-yl)ethyl, 2-(cycloheptanethion-2-yl)ethyl, 2-(cyclooctanethion-2-yl)ethyl, 3-(cyclobutanon-2-yl)propyl, 3-(cyclobutanon-3-yl)propyl, 3-(cyclopentanon-2-yl)propyl, 3-(cyclopentanon-3-yl)propyl, 3-(cyclohexanon-2-yl)propyl, 3-(cyclohexanon-4-yl)propyl, 3-(cycloheptanon-2-yl)propyl, 3-(cyclooctanon-2-yl)propyl, 3-(cyclobutanethion-2-yl)propyl, 3-(cyclobutanethion-3-yl)propyl, 3-(cyclopentanethion-2-yl)-propyl, 3-(cyclopentanethion-3-yl)propyl, 3-(cyclohexanethion-2-yl)propyl, 3-(cyclohexanethion-4-yl)propyl, 3-(cycloheptanethion-2-yl)propyl, 3-(cyclooctanethion-2-yl)propyl, 4-(cyclobutanon-2-yl)butyl, 4-(cyclobutanon-3-yl)-butyl, 4-(cyclopentanon-2-yl)butyl, 4-(cyclopentanon-3-yl)butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl)butyl, 4-(cyclobutanethion-3-yl)butyl, 4-(cyclopentanethion-2-yl)butyl, 4-(cyclopentanethion-3-yl)butyl, 4-(cyclohexanethion-2-yl)butyl, 4-(cyclohexanethion-4-yl)butyl, 4-(cycloheptanethion-2-yl)butyl or 4-(cyclooctanethion-2-yl)butyl, preferably cyclopentanon-2-ylmethyl, cyclohexanon-2-ylmethyl, 2-(cyclopentanon-2-yl)ethyl or 2-(cyclohexanon-2-yl)ethyl;

3- to 7-membered heterocyclyl is to be understood as meaning both saturated, partially or fully unsaturated and aromatic heterocycles having one to three hetero atoms selected from the group consisting of one to three nitrogen atoms, one or two oxygen and one or two sulfur atoms.

Examples of saturated heterocycles which can contain a carbonyl or thiocarbonyl ring member are:

oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydro-pyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1, 3-dioxepan-6-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles which can contain a carbonyl or thiocarbonyl ring member are:

dihydrofuran-2-yl, 1,2-oxazolin-3-yl, 1,2-oxazolin-5-yl, 1,3-oxazolin-2-yl;

Preferred heteroaromatic radicals are those which have 5 or 6 members, eg.

furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2, 4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

With a view to the use of the substituted 4,5-di (trifluoromethyl)pyrazoles I as herbicides, preferred compounds I are those where the substituents have the following meanings, in each case alone or in combination:

$R^1$ is $C_1$–$C_4$-alkyl, in particular methyl;

$R^2$ is hydrogen, fluorine or chlorine;

$R^3$ is cyano, halogen or trifluoromethyl, in particular chlorine;

$R^4$ is hydrogen, nitro, cyano, halogen, —O—$X^2$—Rs, —O—CO—$X^2$—RS, —N($X^2$—$R^5$) ($X^3$—$R^6$), —N($X^2$—$R^5$)—$SO_2$—$X^3$—$R^6$, —N($SO_2$—$X^2$—$R^5$, —N($X^2$—$R^5$)(CO—$X^3$—$R^6$), —S—$X^2$—$R^5$, —SO—$X^2$—$R^5$, —$SO_2$—$X^2$—$R^5$, —$SO_2$—O—$X^2$—$R^5$, —$SO_2$—N($X^2$—$R^5$) ($X^3$—$R^6$), —CO(=NOR$^7$)—$X^2$—$R^5$, or —CO—O—$X^2$—$R^5$ oder —CO—N($X^2$—$R^5$) ($X^3$—$R^6$), in particular hydrogen, nitro, halogen, —N($X^2$—$R^5$) ($X^3$—$R^6$), —N( $X^2$—$R^5$)—$SO_2$—$X^3$—$R^6$, —N($SO_2$—$X^2$—$R^5$) ($SO_2$—$X^3$—$R^6$), —N($X^2$—$R^5$) (CO—$X^3$—$R^6$), —S—$X^2$—$R^5$, —SO—$X^2$—$R^5$, —$SO_2$—$X^2$—$R^5$, —$SO_2$—O—$X^2$—$R^5$, —$SO_2$—N ($X^2$—$R^5$) ($X^3$—$R^6$), —CO—O—$X^2$—$R^5$ or —CO—N($X^2$—$R^5$)($X^3$—$R^6$);

$X^1$ is a chemical bond or an ethene-1,2-diyl, methylene or ethylene chain which can be in each case unsubstituted or have attached to it a halogen or $C_1$–$C_4$-alkyl substituent, in particular a chemical bond, a methylene chain, $CH_2$—CH(halo)— or —CH=C(halo)—;

$X^2$, $X^3$ independently of one another are a chemical bond or a methylene or ethylene chain, each of which can be unsubstituted or have attached to it one or two of the following substituents: halogen, cyano, $C_1$–$C_4$-alkyl and/or $C_1$–$C_4$-haloalkyl, in particular a chemical bond or a methylene chain;

$R^5$ and $R^6$ independently of one another are —Z—$R^8$, hydrogen, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl, $C_3$–$C_8$-cycloalkyl which can contain a carbonyl or thiocarbonyl ring member, phenyl or 3- to 7-membered heterocyclyl which can contain a carbonyl or thiocarbonyl ring member, it being possible for the cycloalkyl rings, the phenyl ring and the heterocyclyl rings to be unsubstituted or to have attached to them one or two substituents, in each case selected from the group consisting of halogen, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy and ($C_1$–$C_4$-alkoxy)carbonyl;

in particlar —Z—$R^8$, hydrogen, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl or phenyl which can be unsubstituted or have attached to it one or two substituents, selected from the group consisting of halogen, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy and ($C_1$–$C_4$-alkoxy)carbonyl;

very especially preferably hydrogen, $C_1$–$C_4$-alkyl, $C_1$–$C_4$-halogenalkyl, $C_2$–$C_4$-alkenyl or $C_2$–$C_4$-alkynyl;

$R^7$ is hydrogen or $C_1$–$C_4$-alkyl;

Z is methylene which can be unsubstituted or substituted by $C_1$–$C_4$-alkyl, $C_1$–$C_4$-alkoxy-$C_1$–$C_4$-alkyl, $C_1$–$C_4$-alkylthio-$C_1$–$C_4$-alkyl or ($C_1$–$C_4$-alkoxy)carbonyl-$C_1$–$C_4$-alkyl, in particular methylene or methylene which is substituted by $C_1$–$C_4$-alkyl;

$R^8$ is nitro, cyano, —$OR^9$, —$N(R^9)R^{10}$, —$SR^9$, —$SO_2$—$R^9$, —CO—$R^9$, —C(=$NOR^{11}$)—$R^5$, —CO—$OR^9$, —CO—N($R^9$)$R^{10}$ or —CO—N($R^9$)—$OR^{10}$, in particular —$OR^9$, —$N(R^{10})R^{10}$, —$SR^9$ or —CO—$OR^9$; very especially preferably —CO—$OR^9$;

$R^9$, $R^{10}$ independently of one another are hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, $C_3$–$C_8$-cycloalkyl-$C_1$–$C_4$-alkyl or phenyl, in particular hydrogen or $C_1$–$C_6$-alkyl;

$R^{11}$ is hydrogen or $C_1$–$C_4$-alkyl.

Very especially preferred are the compounds Ia (≙ I where $R^1$=methyl; $R^2$=hydrogen; $R^3$=chlorine) which are listed in Table 1 below:

TABLE 1

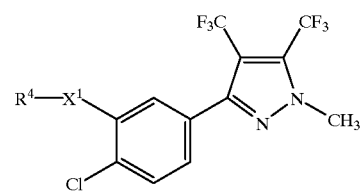

Ia

| No. | —$X^1$—$R^4$ |
|---|---|
| Ia.001 | —H |
| Ia.002 | —$CH_3$ |
| Ia.003 | —$NO_2$ |
| Ia.004 | —CN |
| Ia.005 | —F |
| Ia.006 | —Cl |
| Ia.007 | —Br |
| Ia.008 | —OH |
| Ia.009 | —$OCH_3$ |
| Ia.010 | —OCH($CH_3$)$_2$ |
| Ia.011 | —$OCH_2$—C≡CH |
| Ia.012 | —OCH($CH_3$)—C≡CH |
| Ia.013 | —$OCH_2$—CO—$OCH_3$ |
| Ia.014 | —O-Cyclopentyl |
| Ia.015 | —$OCH_2$-Phenyl |
| Ia.016 | —O—CO—$CH_3$ |
| Ia.017 | —$CH_2$—OH |
| Ia.018 | —$CH_2$—$OCH_3$ |
| Ia.019 | —$CH_2$—$OCH_2$—CO—$OCH_3$ |
| Ia.020 | —$CH_2$—O—CO—$CH_3$ |
| Ia.021 | —$CH_2$—O-cylopentyl |
| Ia.022 | —$CH_2$—$OCH_2$-phenyl |
| Ia.023 | —$NH_2$ |
| Ia.024 | —NH—$CH_3$ |
| Ia.025 | —N($CH_3$)$_2$ |
| Ia.026 | —NH—CO—$CH_3$ |
| Ia.027 | —N($SO_2$—$CH_3$)$_2$ |
| Ia.028 | —NH—$SO_2$—$CH_3$ |
| Ia.029 | —$CH_2$—N($CH_3$)$_2$ |
| Ia.030 | —$CH_2$—NH—$CH_2$—CO—$OCH_3$ |
| Ia.031 | —NH—OH |
| Ia.032 | —N($CH_3$)—$OCH_3$ |
| Ia.033 | —$CH_2$—NH—OH |
| Ia.034 | —$CH_2$—N($CH_3$)—$OCH_3$ |
| Ia.035 | —SH |
| Ia.036 | —$SCH_3$ |
| Ia.037 | —$CH_2$—$SCH_3$ |
| Ia.038 | —SO—$CH_3$ |
| Ia.039 | —$SO_2$—$CH_3$ |
| Ia.040 | —$SO_2$—OH |
| Ia.041 | —$SO_2$—$OCH_3$ |
| Ia.042 | —$SO_2$—$NH_2$ |
| Ia.043 | —$SO_2$—NH—$CH_3$ |
| Ia.044 | —$SO_2$—N($CH_3$)$_2$ |
| Ia.045 | —CHO |
| Ia.046 | —CO—$CH_3$ |
| Ia.047 | —CO-(2-methoxycarbonylpyrrolidin-1-yl) |
| Ia.048 | —CH(=N—OH) |
| Ia.049 | —CH(=N—$OCH_3$) |
| Ia.050 | —CO—OH |
| Ia.051 | —CO—$OCH_3$ |
| Ia.052 | —CO—$OC_2H_5$ |
| Ia.053 | —CO—OCH($CH_3$)$_2$ |
| Ia.054 | —CO—$OCH_2$—CO—$OCH_3$ |
| Ia.055 | —CO—O-cylopentyl |
| Ia.056 | —CO—O-phenyl |
| Ia.057 | —CO—$OCH_2$-phenyl |
| Ia.058 | —CO—$OCH_2$-(2-oxiranyl) |
| Ia.059 | —CO—O-(3-acetoxytetrahydrofuran-4-yl) |
| Ia.060 | —CO—$OCH_2$-(morpholin-4-yl) |
| Ia.061 | —$CH_2$—CH(Cl)—CO—$OCH_3$ |
| Ia.062 | —$CH_2$—CH(Cl)—CO—$OC_2H_5$ |
| Ia.063 | —$CH_2$—CH(Cl)—CO—OC($CH_3$)$_3$ |
| Ia.064 | —$CH_2$—CH(Cl)—CO—$OCH_2$—CO—$OCH_3$ |
| Ia.065 | —$CH_2$—CH(Br)—CO—$OCH_3$ |
| Ia.066 | —$CH_2$—CH(Br)—CO—$OC_2H_5$ |

TABLE 1-continued $$\text{[Structure: Ia - pyrazole with } F_3C, CF_3, CH_3 \text{ groups, phenyl with Cl and } R^4-X^1 \text{ substituents]}$$

| No. | —X$^1$—R$^4$ |
|---|---|
| Ia.067 | —CH$_2$—CH(Br)—CO—OC(CH$_3$)$_3$ |
| Ia.068 | —CH$_2$—CH(Br)—CO—OCH$_2$—CO—OCH$_3$ |
| Ia.069 | —CH$_2$—CH(CN)—CO—OCH$_3$ |
| Ia.070 | —CH$_2$—CH(CN)—CO—OC$_2$H$_5$ |
| Ia.071 | —CH$_2$—CH(CN)—CO—OC(CH$_3$)$_3$ |
| Ia.072 | —CH$_2$—CH(CN)—CO—OCH$_2$—CO—OCH$_3$ |
| Ia.073 | —CH$_2$—CH(OH)—CO—OCH$_3$ |
| Ia.074 | —CH$_2$—CH(OH)—CO—OC$_2$H$_5$ |
| Ia.075 | —CH$_2$—CH(OH)—CO—OC(CH$_3$)$_3$ |
| Ia.076 | —CH$_2$—CH(OH)—CO—OCH$_2$—CO—OCH$_3$ |
| Ia.077 | —CH═C(Cl)—CO—OCH$_3$ |
| Ia.078 | —CH═C(Cl)—CO—OC$_2$H$_5$ |
| Ia.079 | —CH═C(Cl)—CO—OC(CH$_3$)$_3$ |
| Ia.080 | —CH═C(Cl)—CO—OCH$_2$—CO—OCH$_3$ |
| Ia.081 | —CH═C(Br)—CO—OCH$_3$ |
| Ia.082 | —CH═C(Br)—CO—OC$_2$H$_5$ |
| Ia.083 | —CH═C(Br)—CO—OC(CH$_3$)$_3$ |
| Ia.084 | —CH═C(Br)—CO—OCH$_2$—CO—OCH$_3$ |
| Ia.085 | —CH═C(CN)—CO—OCH$_3$ |
| Ia.086 | —CH═C(CN)—CO—OC$_2$H$_5$ |
| Ia.087 | —CH═C(CN)—CO—OC(CH$_3$)$_3$ |
| Ia.088 | —CH═C(CN)—CO—OCH$_2$—CO—OCH$_3$ |
| Ia.089 | —CO—SCH$_3$ |
| Ia.090 | —CO—SC$_2$H$_5$ |
| Ia.091 | —CO—NH$_2$ |
| Ia.092 | —CO—NH—CH$_3$ |
| Ia.093 | —CO—N(CH$_3$)$_2$ |
| Ia.094 | —CO—NH—CH$_2$—CO—OCH$_3$ |
| Ia.095 | —CO—N(CH$_3$)—CH$_2$—CO—OCH$_3$ |
| Ia.096 | —CH$_2$—CH(Cl)—CO—NH$_2$ |
| Ia.097 | —CH$_2$—CH(Cl)—CO—NH—CH$_3$ |
| Ia.098 | —CH$_2$—CH(Cl)—CO—N(CH$_3$)$_2$ |
| Ia.099 | —CH$_2$—CH(Cl)—CO—NH—CH$_2$—CO—OCH$_3$ |
| Ia.100 | —CH$_2$—CH(Cl)—CO—N(CH$_3$)—CH$_2$—CO—OCH$_3$ |
| Ia.101 | —CH$_2$—CH(Br)—CO—NH$_2$ |
| Ia.102 | —CH$_2$—CH(Br)—CO—NH—CH$_3$ |
| Ia.103 | —CH$_2$—CH(Br)—CO—N(CH$_3$)$_2$ |
| Ia.104 | —CH$_2$—CH(Br)—CO—NH—CH$_2$—CO—OCH$_3$ |
| Ia.105 | —CH$_2$—CH(Br)—CO—N(CH$_3$)—CH$_2$—CO—OCH$_3$ |
| Ia.106 | —CH$_2$—CH(CN)—CO—NH$_2$ |
| Ia.107 | —CH$_2$—CH(CN)—CO—NH—CH$_3$ |
| Ia.108 | —CH$_2$—CH(CN)—CO—N(CH$_3$)$_2$ |
| Ia.109 | —CH$_2$—CH(CN)—CO—NH—CH$_2$—CO—OCH$_3$ |
| Ia.110 | —CH$_2$—CH(CN)—CO—N(CH$_3$)—CH$_2$—CO—OCH$_3$ |
| Ia.111 | —CH═C(Cl)—CO—NH$_2$ |
| Ia.112 | —CH═C(Cl)—CO—NH—CH$_3$ |
| Ia.113 | —CH═C(Cl)—CO—N(CH$_3$)$_2$ |
| Ia.114 | —CH═C(Cl)—CO—NH—CH$_2$—CO—OCH$_3$ |
| Ia.115 | —CH═C(Cl)—CO—N(CH$_3$)—CH$_2$—CO—OCH$_3$ |
| Ia.116 | —CH═C(Br)—CO—NH$_2$ |
| Ia.117 | —CH═C(Br)—CO—NH—CH$_3$ |
| Ia.118 | —CH═C(Br)—CO—NH(CH$_3$)$_2$ |
| Ia.119 | —CH═C(Br)—CO—NH—CH$_2$—CO—OCH$_3$ |
| Ia.120 | —CH═C(Br)—CO—N(CH$_3$)—CH$_2$—CO—OCH$_3$ |
| Ia.121 | —CH═C(CN)—CO—NH$_2$ |
| Ia.122 | —CH═C(CN)—CO—NH—CH$_3$ |
| Ia.123 | —CH═C(CN)—CO—N(CH$_3$)$_2$ |
| Ia.124 | —CH═C(CN)—CO—NH—CH$_2$—CO—OCH$_3$ |
| Ia.125 | —CH═C(CN)—CO—N(CH$_3$)—CH$_2$—CO—OCH$_3$ |
| Ia.126 | —CO—NH—OH |
| Ia.127 | —CO—N(CH$_3$)—OCH$_3$ |
| Ia.128 | —OC$_2$H$_5$ |
| Ia.129 | —O-n-C$_3$H$_7$ |
| Ia.130 | —O-n-C$_4$H$_9$ |
| Ia.131 | —OCH$_2$—CH(CH$_3$)$_2$ |
| Ia.132 | —OCH(CH$_3$)—C$_2$H$_5$ |
| Ia.133 | —OC(CH$_3$)$_3$ |
| Ia.134 | —OCH$_2$—CH═CH$_2$ |
| Ia.135 | —OCH$_2$—CH═CH—CH$_3$ |
| Ia.136 | —OCH$_2$—CH$_2$—CH═CH$_2$ |
| Ia.137 | —OCH(CH$_3$)—CH═CH$_2$ |
| Ia.138 | —OCH$_2$—OCH$_3$ |
| Ia.139 | —OCH$_2$—CH$_2$—OCH$_3$ |
| Ia.140 | —OCH$_2$—CN |
| Ia.141 | —OCH$_2$—CH$_2$F |
| Ia.142 | —OCH$_2$—CF$_3$ |
| Ia.143 | —OCH$_2$—CH$_2$Cl |
| Ia.144 | —OCH$_2$—CO—OC$_2$H$_5$ |
| Ia.145 | —OCH$_2$—CO—N(CH$_3$)$_2$ |
| Ia.146 | —OCH(CH$_3$)—CO—OCH$_3$ |
| Ia.147 | —OCH(CH$_3$)—CO—OC$_2$H$_5$ |
| Ia.148 | —OCH(CH$_3$)—CO—N(CH$_3$)$_2$ |
| Ia.149 | —O-cylobutyl |
| Ia.150 | —O-cylohexyl |
| Ia.151 | —OCH$_2$-cylobutyl |
| Ia.152 | —OCH$_2$-cylopentyl |
| Ia.153 | —OCH$_2$-cylohexyl |
| Ia.154 | —O—CO—C$_2$H$_5$ |
| Ia.155 | —C—CO-n-C$_3$H$_7$ |
| Ia.156 | —0—CO-n-C$_4$H$_9$ |
| Ia.157 | —O—CO—CH(CH$_3$)$_2$ |
| Ia.158 | —O—CO—CH$_2$—CH(CH$_3$)$_2$ |
| Ia.159 | —O—CO—CH(CH$_3$)—C$_2$H$_5$ |
| Ia.160 | —O—CO—C(CH$_3$)$_3$ |
| Ia.161 | —O—CO—CH$_2$Cl |
| Ia.162 | —O—CO—CH$_2$—OCH$_3$ |
| Ia.163 | —O—CO-cylobutyl |
| Ia.164 | —O—CO-cylopentyl |
| Ia.165 | —O—CO-cylohexyl |
| Ia.166 | —O—CO-phenyl |
| Ia.167 | —NH—C$_2$H$_5$ |
| Ia.168 | —N(C$_2$H$_5$)$_2$ |
| Ia.169 | —NH-n-C$_3$H$_7$ |
| Ia.170 | —N(n-C$_3$H$_7$)$_2$ |
| Ia.171 | —NH-n-C$_4$H$_9$ |
| Ia.172 | —N(n-C$_4$H$_9$)$_2$ |
| Ia.173 | —NH—CH(CH$_3$)$_2$ |
| Ia.174 | —N(CH(CH$_3$)$_2$)$_2$ |
| Ia.175 | —NH—CH$_2$—CH(CH$_3$)$_2$ |
| Ia.176 | —N(CH$_2$—CH(CH$_3$)$_2$)$_2$ |
| Ia.177 | —NH—CH$_2$—CH═CH$_2$ |
| Ia.178 | —N(CH$_2$—CH═CH$_2$)$_2$ |
| Ia.179 | —NH—CH$_2$—C≡CH |
| Ia.180 | —N(CH$_2$—C≡CH)$_2$ |
| Ia.181 | —NH—CO—C$_2$H$_5$ |
| Ia.182 | —NH—CO-n-C$_3$H$_7$ |
| Ia.183 | —NH—CO-n-C$_4$H$_9$ |
| Ia.184 | —NH—CO—CH(CH$_3$)$_2$ |
| Ia.185 | —NH—CO—CH$_2$—CH(CH$_3$)$_2$ |
| Ia.186 | —NH—CO—CH(CH$_3$)—C$_2$H$_5$ |
| Ia.187 | —NH—CO—C(CH$_3$)$_3$ |
| Ia.188 | —NH—CO—CH$_2$Cl |
| Ia.189 | —NH—CO—CH$_2$—OCH$_3$ |
| Ia.190 | —NH—CO-cylobutyl |
| Ia.191 | —NH—CO-cylopentyl |
| Ia.192 | —NH—CO-cylohexyl |
| Ia.193 | —NH—CO-phenyl |
| Ia.194 | —N(SO$_2$—C$_2$H$_5$)$_2$ |
| Ia.195 | —NH—SO$_2$—C$_2$H$_5$ |
| Ia.196 | —N(SO$_2$-n-C$_3$H$_7$)$_2$ |
| Ia.197 | —NH—SO$_2$-n-C$_3$H$_7$ |
| Ia.198 | —N(SO$_2$-n-C$_4$H$_9$)$_2$ |

TABLE 1-continued

Ia

| No. | —X¹—R⁴ |
|---|---|
| Ia.199 | —NH—SO₂-n-C₄H₉ |
| Ia.200 | —N(SO₂—CH(CH₃)₂)₂ |
| Ia.201 | —NH—SO₂—CH(CH₃)₂ |
| Ia.202 | —N(SO₂—CH₂—CH(CH₃)₂)₂ |
| Ia.203 | —NH—SO₂—CH₂—CH(CH₃)₂ |
| Ia.204 | —N(SO₂—CH₂Cl)₂ |
| Ia.205 | —NH—SO₂—CH₂Cl |
| Ia.206 | —N(SO₂—CH₂Cl)₂ |
| Ia.207 | —NH—SO₂—CH₂Cl |
| Ia.208 | —N(SO₂-phenyl)₂ |
| Ia.209 | —NH—SO₂-phenyl |
| Ia.210 | —N(SO₂—CH₂-phenyl)₂ |
| Ia.211 | —NH—SO₂—CH₂-phenyl |
| Ia.212 | —SC₂H₅ |
| Ia.213 | —S-n-C₃H₇ |
| Ia.214 | —S-n-C₄H₉ |
| Ia.215 | —SCH(CH₃)₂ |
| Ia.216 | —SCH₂—CH(CH₃)₂ |
| Ia.217 | —SCH(CH₃)—C₂H₅ |
| Ia.218 | —SC(CH₃)₃ |
| Ia.219 | —SCH₂—CH=CH₂ |
| Ia.220 | —SCH₂—CH=CH—CH₃ |
| Ia.221 | —SCH(CH₃)—CH=CH₂ |
| Ia.222 | —SCH(CH₃)—CH=CH₂ |
| Ia.223 | —SCH₂—C≡CH |
| Ia.224 | —SCH(CH₃)—C≡CH |
| Ia.225 | —SCH₂—OCH₃ |
| Ia.226 | —SCH₂—CH₂—OCH₃ |
| Ia.227 | —SCH₂—CN |
| Ia.228 | —SCH₂—CH₂F |
| Ia.229 | —SCH₂—CF₃ |
| Ia.230 | —SCH₂—CH₂Cl |
| Ia.231 | —SCH₂—CO—OCH₃ |
| Ia.232 | —SCH₂—CO—OC₂H₅ |
| Ia.233 | —SCH₂—CO—N(CH₃)₂ |
| Ia.234 | —SCH(CH₃)—CO—OCH₃ |
| Ia.235 | —SCH(CH₃)—CO—OC₂H₅ |
| Ia.236 | —SCH(CH₃)—CO—N(CH₃)₂ |
| Ia.237 | —S-cylobutyl |
| Ia.238 | —S-cylopentyl |
| Ia.239 | —S-cylohexyl |
| Ia.240 | —SCH₂-cylobutyl |
| Ia.241 | —SCH₂-cylopentyl |
| Ia.242 | —SCH₂-cylohexyl |
| Ia.243 | —SCH₂-phenyl |
| Ia.244 | —S—CO—CH₃ |
| Ia.245 | —S—CO—C₂H₅ |
| Ia.246 | —S—CO-n-C₃H₇ |
| Ia.247 | —S—CO-n-C₄H₉ |
| Ia.248 | —S—CO—CH(CH₃)₂ |
| Ia.249 | —S—CO—CH₂—CH(CH₃)₂ |
| Ia.250 | —S—CO—CH(CH₃)—C₂H₅ |
| Ia.251 | —S—CO—C(CH₃)₃ |
| Ia.252 | —S—CO—CH₂Cl |
| Ia.253 | —S—CO—CH₂—OCH₃ |
| Ia.254 | —S—CO-cylobutyl |
| Ia.255 | —S—CO-cylopentyl |
| Ia.256 | —S—CO-cylohexyl |
| Ia.257 | —S—CO-phenyl |
| Ia.258 | —SO—C₂H₅ |
| Ia.259 | —SO-n-C₃H₇ |
| Ia.260 | —SO-n-C₄H₉ |
| Ia.261 | —SO—CH(CH₃)₂ |
| Ia.262 | —SO—CH₂—CH(CH₃)₂ |
| Ia.263 | —SO—CH(CH₃)—C₂H₅ |
| Ia.264 | —SO—C(CH₃)₃ |
| Ia.265 | —SO—CH₂—CH=CH₂ |
| Ia.266 | —SO—CH₂—C≡CH |
| Ia.267 | —SO₂—C₂H₅ |
| Ia.268 | —SO₂-n-C₃H₇ |
| Ia.269 | —SO₂-n-C₄H₉ |
| Ia.270 | —SO₂—CH(CH₃)₂ |
| Ia.271 | —SO₂—CH₂—CH(CH₃)₂ |
| Ia.272 | —SO₂—CH(CH₃)—C₂H₅ |
| Ia.273 | —SO₂—C(CH₃)₃ |
| Ia.274 | —SO₂—CH₂—CH=CH₂ |
| Ia.275 | —SO₂—CH₂—C≡CH |
| Ia.276 | —SO₂—OC₂H₅ |
| Ia.277 | —SO₂—O-n-C₃H₇ |
| Ia.278 | —SO₂—O-n-C₄H₉ |
| Ia.279 | —SO₂—OCH(CH₃)₂ |
| Ia.280 | —SO₂—OCH₂—CH(CH₃)₂ |
| Ia.281 | —SO₂—OCH(CH₃)—C₂H₅ |
| Ia.282 | —SO₂—OC(CH₃)₃ |
| Ia.283 | —SO₂—OCH₂—CH=CH₂ |
| Ia.284 | —SO₂—OCH₂—C≡CH |
| Ia.285 | —SO₂—O-cylobutyl |
| Ia.286 | —SO₂—O-cylopentyl |
| Ia.287 | —SO₂—O-cylohexyl |
| Ia.288 | —SO₂—O-phenyl |
| Ia.289 | —SO₂—OCH₂-phenyl |
| Ia.290 | —SO₂—NH—C₂H₅ |
| Ia.291 | —SO₂—N(C₂H₅)₂ |
| Ia.292 | —SO₂—NH-n-C₃H₇ |
| Ia.293 | —SO₂—N(n—C₃H₇)₂ |
| Ia.294 | —SO₂—NH-n-C₄H₉ |
| Ia.295 | —SO₂—N(n—C₄H₉)₂ |
| Ia.296 | —SO₂—NH—CH₂—CO—OCH₃ |
| Ia.297 | —SO₂—NH—CH₂—CO—OC₂H₅ |
| Ia.298 | —SO₂—N(CH₃)—CH₂—CO—OCH₃ |
| Ia.299 | —SO₂—N(CH₃)—CH₂—CO—OC₂H₅ |
| Ia.300 | —SO₂—NH-cylobutyl |
| Ia.301 | —SO₂—NH-cylopentyl |
| Ia.302 | —SO₂—NH-cylohexyl |
| Ia.303 | —SO₂—NH-phenyl |
| Ia.304 | —SO₂—NH—CH₂-phenyl |
| Ia.305 | —CO—C₂H₅ |
| Ia.306 | —CO-n-C₃H₇ |
| Ia.307 | —CO-n-C₄H₉ |
| Ia.308 | —CO—CH(CH₃)₂ |
| Ia.309 | —CO—CH₂—CH(CH₃)₂ |
| Ia.310 | —CO—CH(CH₃)—CH₂—CH₃ |
| Ia.311 | —CO—C(CH₃)₃ |
| Ia.312 | —CO—CH₂Cl |
| Ia.313 | —CO-cylobutyl |
| Ia.314 | —CO-cylopentyl |
| Ia.315 | —CO-cylohexyl |
| Ia.316 | —CO-phenyl |
| Ia.317 | —CH(=N—OC₂H₅) |
| Ia.318 | —CH(=N—O-n-C₃H₇) |
| Ia.319 | —CH(=N—O-n-C₄H₉) |
| Ia.320 | —CH[=N—OCH(CH₃)₂] |
| Ia.321 | —CH[=N—OCH₂—CH(CH₃)₂] |
| Ia.322 | —CH[=N—OCH(CH₃)—C₂H₅] |
| Ia.323 | —CH[=N—OC(CH₃)₃] |
| Ia.224 | —CH(=N—OCH₂—OCH₃) |
| Ia.325 | —CH(=N—O-cylobutyl) |
| Ia.326 | —CH(=N—O-cylopentyl) |
| Ia.327 | —CH(=N—O-cylohexyl) |
| Ia.328 | —CH(=N—O-phenyl) |
| Ia.329 | —CH(=N—OCH₂-phenyl) |
| Ia.330 | —CO—O-n-C₃H₇ |

TABLE 1-continued $$\text{Structure Ia: pyrazole with } F_3C \text{ and } CF_3 \text{ substituents, N-CH}_3, \text{ phenyl ring with Cl and } R^4-X^1 \text{ substituents}$$

| No. | —X¹—R⁴ |
|---|---|
| Ia.331 | —CO—O-n-C₄H₉ |
| Ia.332 | —CO—OCH₂—CH(CH₃)₂ |
| Ia.333 | —CO—OCH(CH₃)—CH₂—CH₃ |
| Ia.334 | —CO—OC(CH₃)₃ |
| Ia.335 | —CO—OCH₂—CH=CH₂ |
| Ia.336 | —CO—OCH₂—CH=CH—CH₃ |
| Ia.337 | —CO—OCH₂—CH₂—CH=CH₂ |
| Ia.338 | —CO—OCH(CH₃)—CH=CH₂ |
| Ia.339 | —CO—OCH₂—C≡CH |
| Ia.340 | —CO—OCH(CH₃)—C≡CH |
| Ia.341 | —CO—OCH₂—CH₂—OCH₃ |
| Ia.342 | —CO—OCH₂—CN |
| Ia.343 | —CO—OCH₂—CH₂F |
| Ia.344 | —CO—OCH₂—CF₃ |
| Ia.345 | —CO—OCH₂—CH₂Cl |
| Ia.346 | —CO—O-cylobutyl |
| Ia.347 | —CO—O-cylohexyl |
| Ia.348 | —CO—OCH₂-cylobutyl |
| Ia.349 | —CO—OCH₂-cylopentyl |
| Ia.350 | —CO—OCH₂-cyclohexyl |
| Ia.351 | —CO—OCH₂—CO—OC₂H₅ |
| Ia.352 | —CO—OCH₂—CO—N(CH₃)₂ |
| Ia.353 | —CO—OCH(CH₃)—CO—OCH₃ |
| Ia.354 | —CO—OCH(CH₃)—CO—OC₂H₅ |
| Ia.355 | —CO—OCH(CH₃)—CO—N(CH₃)₂ |
| Ia.356 | —CH₂—CH(Cl)—CO—OH |
| Ia.357 | —CH₂—CH(Cl)—CO—O-n-C₃H₇ |
| Ia.358 | —CH₂—CH(Cl)—CO—O-n-C₄H₉ |
| Ia.359 | —CH₂—CH(Cl)—CO—OCH(CH₃)₂ |
| Ia.360 | —CH₂—CH(Cl)—CO—OCH₂—CH(CH₃)₂ |
| Ia.361 | —CH₂—CH(Cl)—CO—OCH(CH₃)—C₂H₅ |
| Ia.362 | —CH₂—CH(Cl)—CO—OCH₂—CH=CH₂ |
| Ia.363 | —CH₂—CH(Cl)—CO—OCH₂—C≡CH |
| Ia.364 | —CH₂—CH(Cl)—CO—OCH₂—CO—OC₂H₅ |
| Ia.365 | —CH₂—CH(Cl)—CO—OCH₂—CO—N(CH₃)₂ |
| Ia.366 | —CH₂—CH(Cl)—CO—OCH(CH₃)—CO—OCH₃ |
| Ia.367 | —CH₂—CH(Cl)—CO—OCH(CH₃)—CO—OC₂H₅ |
| Ia.368 | —CH₂—CH(Cl)—CO—OCH(CH₃)—CO—N(CH₃)₂ |
| Ia.369 | —CH₂—CH(Br)—CO—OH |
| Ia.370 | —CH₂—CH(Br)—CO—O-n-C₃H₇ |
| Ia.371 | —CH₂—CH(Br)—CO—O-n-C₄H₉ |
| Ia.372 | —CH₂—CH(Br)—CO—OCH(CH₃)₂ |
| Ia.373 | —CH₂—CH(Br)—CO—OCH₂—CH(CH₃)₂ |
| Ia.374 | —CH₂—CH(Br)—CO—OCH(CH₃)—C₂H₅ |
| Ia.375 | —CH₂—CH(Br)—CO—OCH₂—CH=CH₂ |
| Ia.376 | —CH₂—CH(Br)—CO—OCH₂—C≡CH |
| Ia.377 | —CH₂—CH(Br)—CO—OCH₂—CO—OC₂H₅ |
| Ia.378 | —CH₂—CH(Br)—CO—OCH₂—CO—N(CH₃)₂ |
| Ia.379 | —CH₂—CH(Br)—CO—OCH(CH₃)—CO—OCH₃ |
| Ia.380 | —CH₂—CH(Br)—CO—OCH(CH₃)—CO—OC₂H₅ |
| Ia.381 | —CH₂—CH(Br)—CO—OCH(CH₃)—CO—N(CH₃)₂ |
| Ia.382 | —CH₂—CH(CN)—CO—OH |
| Ia.383 | —CH₂—CH(CN)—CO—O-n-C₃H₇ |
| Ia.384 | —CH₂—CH(CN)—CO—O-n-C₄H₉ |
| Ia.385 | —CH₂—CH(CN)—CO—OCH(CH₃)₂ |
| Ia.386 | —CH₂—CH(CN)—CO—OCH₂—CH(CH₃)₂ |
| Ia.387 | —CH₂—CH(CN)—CO—OCH(CH₃)—C₂H₅ |
| Ia.388 | —CH₂—CH(CN)—CO—OCH₂—CH=CH₂ |
| Ia.389 | —CH₂—CH(CN)—CO—OCH₂—C≡CH |
| Ia.390 | —CH₂—CH(CN)—CO—OCH₂—CO—OC₂H₅ |
| Ia.391 | —CH₂—CH(CN)—CO—OCH₂—CO—N(CH₃)₂ |
| Ia.392 | —CH₂—CH(CN)—CO—OCH(CH₃)—CO—OCH₃ |
| Ia.393 | —CH₂—CH(CN)—CO—OCH(CH₃)—CO—OC₂H₅ |
| Ia.394 | —CH₂—CH(CN)—CO—OCH(CH₃)—CO—N(CH₃)₂ |
| Ia.395 | —CH=C(Cl)—CO—OH |
| Ia.396 | —CH=C(Cl)—CO—O-n-C₃H₇ |
| Ia.397 | —CH=C(Cl)—CO—O-n-C₄H₉ |
| Ia.398 | —CH=C(Cl)—CO—OCH(CH₃)₂ |
| Ia.399 | —CH=C(Cl)—CO—OCH₂—CH(CH₃)₂ |
| Ia.400 | —CH=C(Cl)—CO—OCH(CH₃)—C₂H₅ |
| Ia.401 | —CH=C(Cl)—CO—OCH₂—CH=CH₂ |
| Ia.402 | —CH=C(Cl)—CO—OCH₂—C≡CH |
| Ia.403 | —CH=C(Cl)—CO—OCH₂—CO—OC₂H₅ |
| Ia.404 | —CH=C(Cl)—CO—OCH₂—CO—N(CH₃)₂ |
| Ia.405 | —CH=C(Cl)—CO—OCH(CH₃)—CO—OCH₃ |
| Ia.406 | —CH=C(Cl)—CO—OCH(CH₃)—CO—OC₂H₅ |
| Ia.407 | —CH=C(Cl)—CO—OCH(CH₃)—CO—N(CH₃)₂ |
| Ia.408 | —CH=C(Br)—CO—OH |
| Ia.409 | —CH=C(Br)—CO—O-n-C₃H₇ |
| Ia.410 | —CH=C(Br)—CO—O-n-C₄H₉ |
| Ia.411 | —CH=C(Br)—CO—OCH(CH₃)₂ |
| Ia.412 | —CH=C(Br)—CO—OCH₂—CH(CH₃)₂ |
| Ia.413 | —CH=C(Br)—CO—OCH(CH₃)—C₂H₅ |
| Ia.414 | —CH=C(Br)—CO—OCH₂—CH=CH₂ |
| Ia.415 | —CH=C(Br)—CO—OCH₂—C≡CH |
| Ia.416 | —CH=C(Br)—CO—OCH₂—CO—OC₂H₅ |
| Ia.417 | —CH=C(Br)—CO—OCH₂—CO—N(CH₃)₂ |
| Ia.418 | —CH=C(Br)—CO—OCH(CH₃)—CO—OCH₃ |
| Ia.419 | —CH=C(Br)—CO—OCH(CH₃)—CO—OC₂H₅ |
| Ia.420 | —CH=C(Br)—CO—OCH(CH₃)—CO—N(CH₃)₂ |
| Ia.421 | —CH=C(CN)—CO—OH |
| Ia.422 | —CH=C(CN)—CO—O-n-C₃H₇ |
| Ia.423 | —CH=C(CN)—CO—O-n-C₄H₉ |
| Ia.424 | —CH=C(CN)—CO—OCH(CH₃)₂ |
| Ia.425 | —CH=C(CN)—CO—OCH₂—CH(CH₃)₂ |
| Ia.426 | —CH=C(CN)—CO—OCH(CH₃)—C₂H₅ |
| Ia.427 | —CH=C(CN)—CO—OCH₂—CH=CH₂ |
| Ia.428 | —CH=C(CN)—CO—OCH₂—C≡CH |
| Ia.429 | —CH=C(CN)—CO—OCH₂—CO—OC₂H₅ |
| Ia.430 | —CH=C(CN)—CO—OCH₂—CO—N(CH₃)₂ |
| Ia.431 | —CH=C(CN)—CO—OCH(CH₃)—CO—OCH₃ |
| Ia.432 | —CH=C(CN)—CO—OCH(CH₃)—CO—OC₂H₅ |
| Ia.433 | —CH=C(CN)—CO—OCH(CH₃)—CO—N(CH₃)₂ |
| Ia.434 | —CO—S-n-C₃H₇ |
| Ia.435 | —CO—S-n-C₄H₉ |
| Ia.436 | —CO—SCH(CH₃)₂ |
| Ia.437 | —CO—SCH₂—CH(CH₃)₂ |
| Ia.438 | —CO—SCH(CH₃)—C₂H₅ |
| Ia.439 | —CO—SC(CH₃)₃ |
| Ia.440 | —CO—SCH₂—CH=CH₂ |
| Ia.441 | —CO—SCH₂—C≡CH |
| Ia.442 | —CO—SCH₂—CO—OCH₃ |
| Ia.443 | —CO—SCH₂—CO—OC₂H₅ |
| Ia.444 | —CO—NH—C₂H₅ |
| Ia.445 | —CO—N(C₂H₅)₂ |
| Ia.446 | —CO—NH-n-C₃H₇ |
| Ia.447 | —CO—N(n-C₃H₇)₂ |
| Ia.448 | —CO—NH-n-C₄H₉ |
| Ia.449 | —CO—N(n-C₄H₉)₂ |
| Ia.450 | —CO—NH—CH(CH₃)₂ |
| Ia.451 | —CO—N(CH(CH₃)₂)₂ |
| Ia.452 | —CO—NH—CH₂—CH(CH₃)₂ |
| Ia.453 | —CO—N[CH₂—CH(CH₃)₂]₂ |
| Ia.454 | —CO—NH—CH₂—CH=CH₂ |
| Ia.455 | —CO—N(CH₂—CH=CH₂)₂ |
| Ia.456 | —CO—NH—CH₂—C≡CH |
| Ia.457 | —CO—N(CH₂—C≡CH)₂ |
| Ia.458 | —CO—NH—CH₂—CO—OC₂H₅ |
| Ia.459 | —CO—N(CH₃)—CH₂—CO—OC₂H₅ |
| Ia.460 | —CO—NH—CH₂—CO—N(CH₃)₂ |
| Ia.461 | —CO—N(CH₃)—CH₂—CO—N(CH₃)₂ |
| Ia.462 | —CO—NH—CH(CH₃)—CO—OCH₃ |

TABLE 1-continued

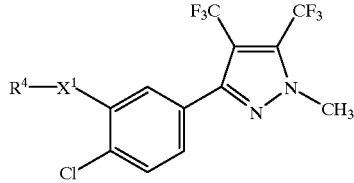

Ia

| No. | —X¹—R⁴ |
|---|---|
| Ia.463 | —CO—N(CH₃)—CH(CH₃)—CO—OCH₃ |
| Ia.464 | —CO—NH—CH(CH₃)—CO—OC₂H₅ |
| Ia.465 | —CO—N(CH₃)—CH(CH₃)—CO—OC₂H₅ |
| Ia.466 | —CO—NH—CH(CH₃)—CO—N(CH₃)₂ |
| Ia.467 | —CO—N(CH₃)—CH(CH₃)—CO—N(CH₃)₂ |
| Ia.468 | —CH₂—CH(Cl)—CO—NH—C₂H₅ |
| Ia.469 | —CH₂—CH(Cl)—CO—N(C₂H₅)₂ |
| Ia.470 | —CH₂—CH(Cl)—CO—NH-n-C₃H₇ |
| Ia.471 | —CH₂—CH(Cl)—CO—N(n—C₃H₇)₂ |
| Ia.472 | —CH₂—CH(Cl)—CO—NH-n-C₄H₉ |
| Ia.473 | —CH₂—CH(Cl)—CO—N(n—C₄H₉)₂ |
| Ia.474 | —CH₂—CH(Cl)—CO—NH—CH₂—CO—OC₂H₅ |
| Ia.475 | —CH₂—CH(Cl)—CO—N(CH₃)—CH₂—CO—OC₂H₅ |
| Ia.476 | —CH₂—CH(Cl)—CO—NH—CH₂—CO—N(CH₃)₂ |
| Ia.477 | —CH₂—CH(Cl)—CO—N(CH₃)—CH₂—CO—N(CH₃)₂ |
| Ia.478 | —CH₂—CH(Cl)—CO—NH—CH(CH₃)—CO—OCH₃ |
| Ia.479 | —CH₂—CH(Cl)—CO—N(CH₃)—CH(CH₃)—CO—OCH₃ |
| Ia.480 | —CH₂—CH(Cl)—CO—NH—CH(CH₃)—CO—OC₂H₅ |
| Ia.481 | —CH₂—CH(Cl)—CO—N(CH₃)—CH(CH₃)—CO—OC₂H₅ |
| Ia.482 | —CH₂—CH(Br)—CO—NH—C₂H₅ |
| Ia.483 | —CH₂—CH(Br)—CO—N(C₂H₅)₂ |
| Ia.484 | —CH₂—CH(Br)—CO—NH-n-C₃H₇ |
| Ia.485 | —CH₂—CH(Br)—CO—N(n—C₃H₇)₂ |
| Ia.486 | —CH₂—CH(Br)—CO—NH-n-C₄H₉ |
| Ia.487 | —CH₂—CH(Br)—CO—N(n—C₄H₉)₂ |
| Ia.488 | —CH₂—CH(Br)—CO—NH—CH₂—CO—OC₂H₅ |
| Ia.489 | —CH₂—CH(Br)—CO—N(CH₃)—CH₂—CO—OC₂H₅ |
| Ia.490 | —CH₂—CH(Br)—CO—NH—CH₂—CO—N(CH₃)₂ |
| Ia.491 | —CH₂—CH(Br)—CO—N(CH₃)—CH₂—CO—N(CH₃)₂ |
| Ia.492 | —CH₂—CH(Br)—CO—NH—CH(CH₃)—CO—OCH₃ |
| Ia.493 | —CH₂—CH(Br)—CO—N(CH₃)—CH(CH₃)—CO—OCH₃ |
| Ia.494 | —CH₂—CH(Br)—CO—NH—CH(CH₃)—CO—OC₂H₅ |
| Ia.495 | —CH₂—CH(Br)—CO—N(CH₃)—CH(CH₃)—CO—OC₂H₅ |
| Ia.496 | —CH₂—CH(CN)—CO—NH—C₂H₅ |
| Ia.497 | —CH₂—CH(CN)—CO—N(C₂H₅)₂ |
| Ia.498 | —CH₂—CH(CN)—CO—NH-n-C₃H₇ |
| Ia.499 | —CH₂—CH(CN)—CO—N(n—C₃H₇)₂ |
| Ia.500 | —CH₂—CH(CN)—CO—NH-n-C₄H₉ |
| Ia.501 | —CH₂—CH(CN)—CO—N(n—C₄H₉)₂ |
| Ia.502 | —CH₂—CH(CN)—CO—NH—CH₂—CO—OC₂H₅ |
| Ia.503 | —CH₂—CH(CN)—CO—N(CH₃)—CH₂—CO—OC₂H₅ |
| Ia.504 | —CH₂—CH(CN)—CO—NH—CH₂—CO—N(CH₃)₂ |
| Ia.505 | —CH₂—CH(CN)—CO—N(CH₃)—CH₂—CO—N(CH₃)₂ |
| Ia.506 | —CH₂—CH(CN)—CO—NH—CH(CH₃)—CO—OCH₃ |
| Ia.507 | —CH₂—CH(CN)—CO—N(CH₃)—CH(CH₃)—CO—OCH₃ |
| Ia.508 | —CH₂—CH(CN)—CO—NH—CH(CH₃)—CO—OC₂H₅ |
| Ia.509 | —CH₂—CH(CN)—CO—N(CH₃)—CH(CH₃)—CO—OC₂H₅ |
| Ia.510 | —CH=C(Cl)—CO—NH—C₂H₅ |
| Ia.511 | —CH=C(Cl)—CO—N(C₂H₅)₂ |
| Ia.512 | —CH=C(Cl)—CO—NH-n-C₃H₇ |
| Ia.513 | —CH=C(Cl)—CO—N(n—C₃H₇)₂ |
| Ia.514 | —CH=C(Cl)—CO—NH-n-C₄H₉ |
| Ia.515 | —CH=C(Cl)—CO—N(n—C₄H₉)₂ |
| Ia.516 | —CH=C(Cl)—CO—NH—CH₂—CO—OC₂H₅ |
| Ia.517 | —CH=C(Cl)—CO—N(CH₃)—CH₂—CO—OC₂H₅ |
| Ia.516 | —CH=C(Cl)—CO—NH—CH₂—CO—N(CH₃)₂ |
| Ia.519 | —CH=C(Cl)—CO—N(CH₃)—CH₂—CO—N(CH₃)₂ |
| Ia.520 | —CH=C(Cl)—CO—NH—CH(CH₃)—CO—OCH₃ |
| Ia.521 | —CH=C(Cl)—CO—N(CH₃)—CH(CH₃)—CO—OCH₃ |
| Ia.522 | —CH=C(Cl)—CO—NH—CH(CH₃)—CO—OC₂H₅ |
| Ia.523 | —CH=C(Cl)—CO—N(CH₃)—CH(CH₃)—CO—OC₂H₅ |
| Ia.524 | —CH=C(Br)—CO—NH—C₂H₅ |
| Ia.525 | —CH=C(Br)—CO—N(C₂H₅)₂ |
| Ia.526 | —CH=C(Br)—CO—NH-n-C₃H₇ |
| Ia.527 | —CH=C(Br)—CO—N(n—C₃H₇)₂ |
| Ia.528 | —CH=C(Br)—CO—NH-n-C₄H₉ |

TABLE 1-continued

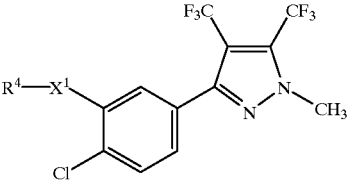

Ia

| No. | —X¹—R⁴ |
|---|---|
| Ia.529 | —CH=C(Br)—CO—N(n—C₄H₉)₂ |
| Ia.530 | —CH=C(Br)—CO—NH—CH₂—CO—OC₂H₅ |
| Ia.531 | —CH=C(Br)—CO—N(CH₃)—CH₂—CO—OC₂H₅ |
| Ia.532 | —CH=C(Br)—CO—NH—CH₂—CO—N(CH₃)₂ |
| Ia.533 | —CH=C(Br)—CO—N(CH₃)—CH₂—CO—N(CH₃)₂ |
| Ia.534 | —CH=C(Br)—CO—NH—CH(CH₃)—CO—OCH₃ |
| Ia.535 | —CH=C(Br)—CO—N(CH₃)—CH(CH₃)—CO—OCH₃ |
| Ia.536 | —CH=C(Br)—CO—NH—CH(CH₃)—CO—OC₂H₅ |
| Ia.537 | —CH=C(Br)—CO—N(CH₃)—CH(CH₃)—CO—OC₂H₅ |
| Ia.538 | —CH=C(CN)—CO—NH—C₂H₅ |
| Ia.539 | —CH=C(CN)—CO—N(C₂H₅)₂ |
| Ia.540 | —CH=C(CN)—CO—NH-n-C₃H₇ |
| Ia.541 | —CH=C(CN)—CO—N(n—C₃H₇)₂ |
| Ia.542 | —CH=C(CN)—CO—NH-n-C₄H₉ |
| Ia.543 | —CH=C(CN)—CO—N(n—C₄H₉)₂ |
| Ia.544 | —CH=C(CN)—CO—NH—CH₂—CO—OC₂H₅ |
| Ia.545 | —CH=C(CN)—CO—N(CH₃)—CH₂—CO—OC₂H₅ |
| Ia.546 | —CH=C(CN)—CO—NH—CH₂—CO—N(CH₃)₂ |
| Ia.547 | —CH=C(CN)—CO—N(CH₃)—CH₂—CO—N(CH₃)₂ |
| Ia.548 | —CH=C(CN)—CO—NH—CH(CH₃)—CO—OCH₃ |
| Ia.549 | —CH=C(CN)—CO—N(CH₃)—CH(CH₃)—CO—OCH₃ |
| Ia.550 | —CH=C(CN)—CO—NH—CH(CH₃)—CO—OC₂H₅ |
| Ia.551 | —CH=C(CN)—CO—N(CH₃)—CH(CH₃)—CO—OC₂H₅ |
| Ia.552 | —CO—NH—OCH₃ |
| Ia.553 | —CO—NH—OC₂H₅ |
| Ia.554 | —CO—N(C₂H₅)—OC₂H₅ |
| Ia.555 | —CH₂—CH(Cl)—CO—NH—OH |
| Ia.556 | —CH₂—CH(Cl)—CO—NH—OCH₃ |
| Ia.557 | —CH₂—CH(Cl)—CO—N(CH₃)—OCH₃ |
| Ia.558 | —CH₂—CH(Cl)—CO—NH—OC₂H₅ |
| Ia.559 | —CH₂—CH(Cl)—CO—N(C₂H₅)—OC₂H₅ |
| Ia.560 | —CH₂—CH(Br)—CO—NH—OH |
| Ia.561 | —CH₂—CH(Br)—CO—NH—OCH₃ |
| Ia.562 | —CH₂—CH(Br)—CO—N(CH₃)—OCH₃ |
| Ia.563 | —CH₂—CH(Br)—CO—NH—OC₂H₅ |
| Ia.564 | —CH₂—CH(Br)—CO—N(C₂H₅)—OC₂H₅ |
| Ia.565 | —CH₂—CH(CN)—CO—NH—OH |
| Ia.566 | —CH₂—CH(CN)—CO—NH—OCH₃ |
| Ia.567 | —CH₂—CH(CN)—CO—N(CH₃)—OCH₃ |
| Ia.568 | —CH₂—CH(CN)—CO—NH—OC₂H₅ |
| Ia.569 | —CH₂—CH(CN)—CO—N(C₂H₅)—OC₂H₅ |
| Ia.570 | —CH=C(Cl)—CO—NH—OH |
| Ia.571 | —CH=C(Cl)—CO—NH—OCH₃ |
| Ia.572 | —CH=C(Cl)—CO—N(CH₃)—OCH₃ |
| Ia.573 | —CH=C(Cl)—CO—NH—OC₂H₅ |
| Ia.574 | —CH=C(Cl)—CO—N(C₂H₅)—OC₂H₅ |
| Ia.575 | —CH=C(Br)—CO—NH—OH |
| Ia.576 | —CH=C(Br)—CO—NH—OCH₃ |
| Ia.577 | —CH=C(Br)—CO—N(CH₃)—OCH₃ |
| Ia.578 | —CH=C(Br)—CO—NH—OC₂H₅ |
| Ia.579 | —CH=C(Br)—CO—N(C₂H₅)—OC₂H₅ |
| Ia.580 | —CH=C(CN)—CO—NH—OH |
| Ia.581 | —CH=C(CN)—CO—NH—OCH₃ |
| Ia.582 | —CH=C(CN)—CO—N(CH₃)—OCH₃ |
| Ia.583 | —CH=C(CN)—CO—NH—OC₂H₅ |
| Ia.584 | —CH=C(CN)—CO—N(C₂H₅)—OC₂H₅ |
| Ia.585 | —SO₂-(pyrrolidin-1-yl) |
| Ia.586 | —SO₂-(piperidin-1-yl) |
| Ia.587 | —SO₂-(2-methoxycarbonylpyrrolidin-1-yl) |
| Ia.588 | —SO₂-(2-methoxycarbonylpiperidin-1-yl) |
| Ia.589 | —CO-(pyrrolidin-1-yl) |
| Ia.590 | —CO-(piperidin-1-yl) |
| Ia.591 | —CO-(2-methoxycarbonylpyrrolidin-1-yl) |
| Ia.592 | —CO-(2-methoxycarbonylpiperidin-1-yl) |
| Ia.593 | —CH₂—CH(Cl)—CO-(pyrrolidin-1-yl) |
| Ia.594 | —CH₂—CH(Cl)—CO-(piperidin-1-yl) |

TABLE 1-continued

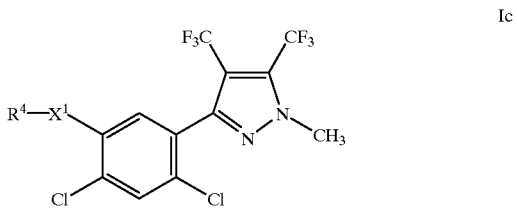

| No. | —X¹—R⁴ |
|---|---|
| Ia.595 | —CH₂—CH(Cl)—CO-(2-methoxycarbonylpyrrolidin-1-yl) |
| Ia.596 | —CH₂—CH(Cl)—CO-(2-methoxycarbonylpiperidin-1-yl) |
| Ia.597 | —CH₂—CH(Br)—CO-(pyrrolidin-1-yl) |
| Ia.598 | —CH₂—CH(Br)—CO-(piperidin-1-y)1 |
| Ia.599 | —CH₂—CH(Br)—CO-(2-methoxycarbonylpyrrolidin-1-yl) |
| Ia.600 | —CH₂—CH(Br)—CO-(2-methoxycarbonylpiperidin-1-yl) |
| Ia.601 | —CH₂—CH(CN)—CO-(pyrrolidin-1-yl) |
| Ia.602 | —CH₂—CH(CN)—CO-(piperidin-1-yl) |
| Ia.603 | —CH₂—CH(CN)—CO-(2-methoxycarbonylpyrrolidin-1-yl) |
| Ia.604 | —CH₂—CH(CN)—CO-(2-methoxycarbonylpiperidin-1-yl) |
| Ia.605 | —CH=C(Cl)—CO-(pyrrolidin-1-yl) |
| Ia.606 | —CH=C(Cl)—CO-(piperidin-1-yl) |
| Ia.607 | —CH=C(Cl)—CO-(2-methoxycarbonylpyrrolidin-1-yl) |
| Ia.608 | —CH=C(Cl)—CO-(2-methoxycarbonylpiperidin-1-yl) |
| Ia.609 | —CH=C(Br)—CO-(pyrrolidin-1-yl) |
| Ia.610 | —CH=C(Br)—CO-(piperidin-1-yl) |
| Ia.611 | —CH=C(Br)—CO-(2-methoxycarbonylpyrrolidin-1-yl) |
| Ia.612 | —CH=C(Br)—CO-(2-methoxycarbonylpiperidin-1-yl) |
| Ia.613 | —CH=C(CN)—CO-(pyrrolidin-1-yl) |
| Ia.614 | —CH=C(CN)—CO-(piperidin-1-yl) |
| Ia.615 | —CH=C(CN)—CO-(2-methoxycarbonylpyrrolidin-1-yl) |
| Ia.616 | —CH=C(CN)—CO-(2-methoxycarbonylpiperidin-1-yl) |

Other especially preferred 4,5-di(trifluoromethyl) pyrazoles of the formulae Ib and Ic are, in particular, the compounds Ib.001–Ib.616, which differ from the corresponding compounds Ia.001–Ia.616 only by the fact that $R^2$ is fluorine:

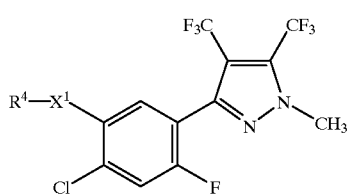

the compounds Ic.001–Ic.616, which differ from the corresponding compounds Ia.001–Ia.616 only by the fact that $R^2$ is chlorine:

Ic

The substituted 4,5-di(trifluoromethyl)pyrazoles of the formula I can be obtained in various ways, in particular by one of the following processes:

A) 1,3-dipolar cycloaddition of nitrile-imines

A.1) Precursor: Preparation of α-halobenzaldehyde hydrazones III in a manner known per se by conversion of benzaldehydes VII into hydrazones VIII and subsequent halogenation of VIII {cf., for example, P. Wolkoff, Can. J. Chem. 53, 1333 (1975) and W. Fliege et al., Chem. Ber. 117, 1194 (1984)}:

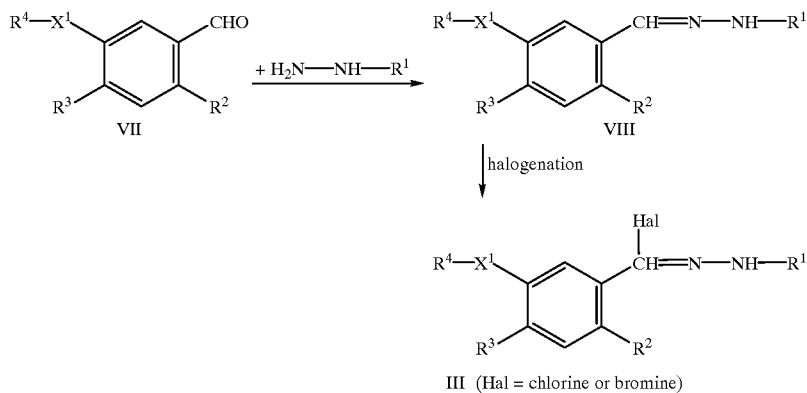

III (Hal = chlorine or bromine)

Suitable halogenating agents are preferably chlorine, bromine, N-chlorosuccinimide and N-bromosuccinimide.

The reaction is normally carried out in an inert organic solvent/diluent, for example an ether such as diethyl ether, methyl tert-butyl ether and tetrahydrofuran, a lower alcohol such as methanol and ethanol, a carboxylic acid such as acetic acid, an aprotic solvent such as acetonitrile and dimethylformamide, or a mixture of these.

As a rule, the process is carried out between the melting and the boiling point of the reaction mixture, in particular at from (−50) to 50° C.

Hydrazine derivative and halogenating agent are generally employed in approximately equimolar amounts or—to obtain as complete as possible a conversion of the starting compound in question—in an excess of up to approx. 5 times the molar amount based on the amount of VII or VIII, respectively.

If desired, the process products III can also be obtained in the form of acid addition salts III·HΨ, Ψ in particular being halide, carboxylate or sulfate.

A.2) Reaction of the benzoic acid halide hydrazonides III with hexafluoro-2-butyne or with a hexafluorobutene derivative IV in the presence of a base:

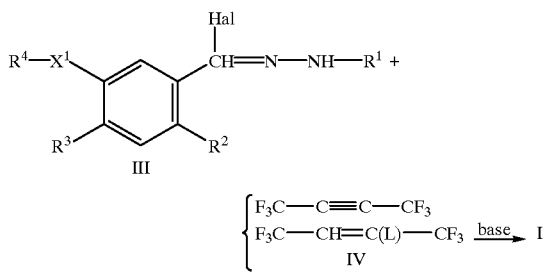

L is a customary leaving group such as halide, carboxylate, mesylate, p-tolylsulfonate (tosylate) or trifluoromethanesulfonate (triflate).

The reaction is normally carried out in an inert organic solvent/diluent, for example in an aromatic hydrocarbon such as n-hexane and toluene, an ether such as diethyl ether, methyl tert-butyl ether and tetrahydrofuran, an ester such as ethyl acetate, or an aprotic solvent such as acetonitrile and dimethylformamide.

Examples of suitable bases are alkali metal hydroxides, alkaline earth metal hydroxides, alkali metal hydrogen carbonates, alkaline earth metal hydrogen carbonates, alkali metal carbonates, alkaline earth metal carbonates and tertiary amines such as triethylamine and pyridine.

As a rule, the process is carried out between the melting and the boiling point of the reaction mixture, in particular at from (−50) to 50° C.

Hexafluoro-2-butyne or IV are generally employed in an approximately equivalent amount or in an excess of up to approx. 5 times the molar amount based on the amount of III.

In order to essentially completely convert III with hexafluoro-2-butyne, it is recommended to use at least one equivalent of base; in contrast, in order essentially completely to convert III with IV it is recommended to employ at least two equivalents of base based on the amount of III. If an excess of base is employed, this normally amounts to up to 5 times the molar amount based on the amount of III.

B) Reactions on the phenyl ring

B.1) nitration of 4,5-di(trifluoromethyl)pyrazoles I where $X^1$—$R^4$ is hydrogen and reaction of the process products to give other compounds of the formula I:

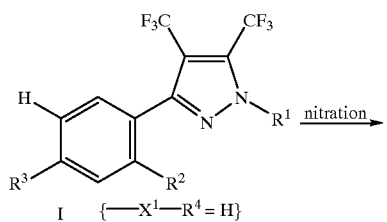

I {—$X^1$—$R^4$ = H}

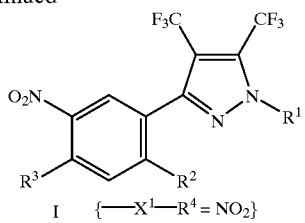

I {—$X^1$—$R^4$ = $NO_2$}

Examples of suitable nitrating reagents are nitric acid in various concentrations, including concentrated and fuming nitric acid, mixtures of sulfuric acid and nitric acid, acetyl nitrates and alkyl nitrates.

The reaction can either be carried out in the absence of a solvent in an excess of the nitrating reagent or else in an inert solvent or diluent, suitable substances being, for example, water, inorganic acids, organic acids, halohydrocarbons such as methylene chloride, anhydrides such as acetic anhydride and mixtures of these.

Starting compound I (—$X^1$—$R^4$=H) and nitrating reagent are expediently employed in approximately equimolar amounts; to optimize the reaction of the starting compound, however, it may be advantageous to use an excess of the nitrating reagent of up to approximately 10 times the molar amount. If the reaction is carried out in the nitrating reagent in the absence of a solvent, the nitrating reagent is present in an even larger excess.

The reaction temperature is normally at from (−100) to 200° C., preferably at from (−30) to 50° C.

The process products where —$X^1$—$R^4NO_2$ can then be reduced to give compounds I where —$X^1$—$R^4$=amino or —NHOH.

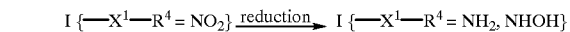

I {—$X^1$—$R^4$ = $NO_2$} reduction→ I {—$X^1$—$R^4$ = $NH_2$, NHOH}

The reduction can be carried out using a metal such as iron, zinc or tin under acidic reaction conditions or using a complex hydride such as lithium aluminum hydride and sodium borohydride, suitable solvents being, for example, water, alcohols such as methanol, ethanol and isopropanol or ethers such as diethyl ether, methyl tert-butyl ether, dioxane, tetrahydrofuran and ethylene glycol dimethyl ether, depending on the reducing agent used.

When carrying out the reduction with a metal, this is preferably done in the absence of a solvent in an inorganic acid, in particular in concentrated or dilute hydrochloric acid, or in an organic acid such as acetic acid. Alternatively, it is possible to admix an inert solvent, eg. one of those mentioned above, with the acid.

The starting compounds I (—$X^1$—$R^4$=$NO_2$) and the reducing agent are expediently employed in approximately equimolar amounts; however, to optimize the course of the reaction it may be advantageous to use an excess of one of the two reactants, of up to approximately 10 times the molar amount.

The amount of acid is not critical. To reduce the starting compound as completely as possible, it is expedient to use at least an equivalent amount of acid.

The reaction temperature is generally at from (−30) to 200° C., preferably at from 0 to 80° C.

For work-up, the reaction mixture is usually diluted with water and the product is isolated by filtration, crystallization or extraction with a solvent which is sparingly miscible with water, eg. with ethyl acetate, diethyl ether or methylene chloride. If desired, the product can subsequently be purified as usual.

The nitro group of the compounds I where —X$^1$—R$^4$= nitro can also be hydrogenated catalytically using hydrogen. Examples of suitable catalysts are Raney nickel, palladium-on-charcoal, palladium oxide, platinum and platinum oxide, an amount of from 0.05 to 10.0 mol % of catalyst based on the compound to be reduced generally being sufficient.

The process is either carried out in the absence of a solvent or in an inert solvent or diluent, eg. in acetic acid, a mixture of acetic acid and water, ethyl acetate, ethanol or in toluene.

After the catalyst has been removed, the reaction solution can be worked up as usual to obtain the product.

The hydrogenation can be carried out under atmospheric pressure or under elevated pressure.

The amino group can subsequently be diazotized in a customary manner. The diazonium salts can then be used for obtaining compounds I where —X$^1$—R$^4$=cyano or halogen {for the Sandmeyer reaction, cf., for example, Houben-Weyl, Methoden der Organischen Chemie [Methods in Organic Chemistry], Georg Thieme Verlag Stuttgart, Vol. 5/4, 4th Edition 1960, p. 438 et seq.}, —X$^1$—R$^4$ hydroxyl {for boiling in phenol, see, for example, Org. Synth. Coll. Vol. 3 (1955), p. 130}, —X$^1$—R$^4$=mercapto or C$_1$–C$_6$-alkylthio {see, in this context, for example Houben-Weyl, Methoden der Organischen Chemie [Methods in Organic Chemistry], Georg Thieme Verlag Stuttgart, Vol. E11 1984, pp. 43 and 176}, —X$^1$—R$^4$=halosulfonyl {cf., in this context, for example Houben-Weyl, Methoden der Organischen Chemie [Methods in Organic Chemistry], Georg Thieme Verlag Stuttgart, Vol. E11 1984, p. 1069 et seq.}, —X$^1$—R$^4$=for example —CH$_2$—CH(halo)—CO—O—X$^2$—R$^5$, —CH=C(halo)—CO—O—X$^2$—R$^5$ {these are, in general, the products of a Meerwein arylation reaction; cf., in this context, for example C.S. Rondestredt, Org. React. 11, 189 (1960) and H. P. Doyle et al., J. Org. Chem. 42, 2431 (1977)}:

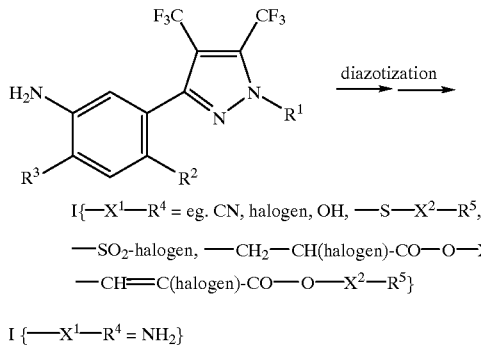

I{—X$^1$—R$^4$ = eg. CN, halogen, OH, —S—X$^2$—R$^5$,

—SO$_2$-halogen, —CH$_2$—CH(halogen)-CO—O—X$^2$—R$^5$,

—CH=C(halogen)-CO—O—X$^2$—R$^5$}

I{—X$^1$—R$^4$ = NH$_2$}

In general, the diazonium salt is obtained in a manner known per se by reacting I where —X$^1$—R$^4$=amino with a nitrite such as sodium nitrite and potassium nitrite in an aqueous acid solution, eg. in hydrochloric acid, hydrobromic acid or sulfuric acid.

Alternatively, it is possible to carry out the process under anhydrous conditions, eg. in hydrogen chloride-containing glacial acetic acid, in absolute alcohol, in dioxans or tetrahydrofuran, in acetonitrile or in acetone, in which case the starting compound (I where —X$^1$—R$^4$=NH$_2$) is treated with a nitrous ester such as tert-butyl nitrite and isopentyl nitrite.

The resulting diazonium salt is particularly preferably converted into the corresponding compound I where —X$^1$—R$^4$=cyano, chlorine, bromine or iodine by treating it with a solution or suspension of a copper(I) salt such as copper(I) cyanide, copper(I) chloride, copper(I) bromide and copper (I) iodide, or else with an alkali metal salt solution.

The resulting diazonium salt is expediently converted into the corresponding compound I where —X$^1$—R$^4$=hydroxyl by treating it with an aqueous acid, preferably sulfuric acid. The addition of a copper(II) salt such as copper(II) sulfate may have an advantageous effect on the course of the reaction.

In general, the process is carried out at from 0 to 100° C., preferably at the boiling point of the reaction mixture.

Compounds I where —X$^1$—R$^4$=mercapto, C$_1$–C$_6$-alkylthio or halosulfonyl are usually obtained by reacting the diazonium salt with hydrogen sulfide, an alkali metal sulfide, a dialkyl disulfide such as dimethyl disulfide, or with sulfur dioxide.

The Meerwein arylation reaction is usually a reaction of the diazonium salts with alkenes or alkynes. The alkene or alkyne is preferably employed in an excess of up to 3000 mol % based on the amount of the diazonium salt.

The above-described reactions of the diazonium salt can be carried out for example in water, in aqueous hydrochloric acid or hydrobromic acid. in a ketone such as acetone, diethyl ketone and methyl ethyl ketone, in a nitrile such as acetonitrile, in an ether such as dioxane and tetrahydrofuran or in an alcohol such as methanol and ethanol.

Unless otherwise specified for the individual reactions, the reaction temperatures are normally at from (–30) to +50° C.

All reactants are preferably employed in approximately stoichiometric amounts, but an excess of one or the other reactant of up to 3000 mol % may also be advantageous.

The compounds I where —X$^1$—R$^4$ mercapto can also be obtained by reducing the corresponding compounds I where —X$^1$—R$^4$=halosulfonyl:

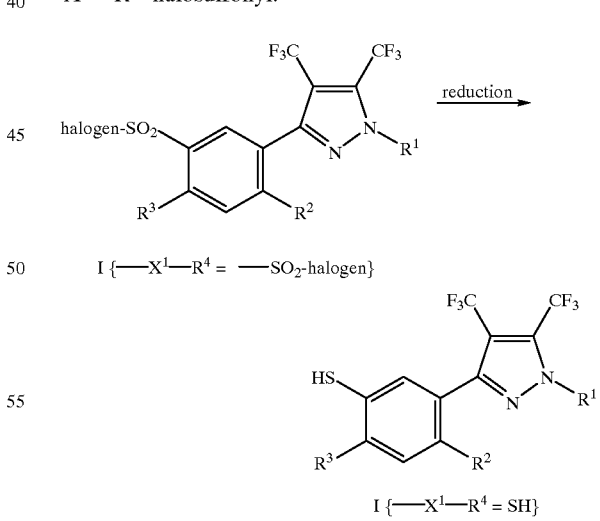

Examples of useful reducing agents are transition metals such as iron, zinc and tin (cf., in this context, for example "The Chemistry of the Thiol Group", John Wiley, 1974, p. 216).

B.2) Halosulfonation of 4,5-di(trifluoromethyl)pyrazoles I where —X$^1$—R$^4$ is hydrogen:

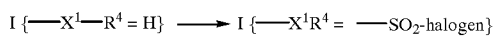

The halosulfonation can be carried out in the absence of a solvent in an excess of sulfonating reagent or in an inert solvent/diluent, eg. in a halogenated hydrocarbon, an ether, an alkylnitrile or a mineral acid.

Chlorosulfonic acid is the preferred reagent and the preferred solvent.

The sulfonating reagent is usually employed in a slightly substoichiometric amount (up to approximately 95 mol %) or in an excess of 1 to 5 times the molar amount based on the starting compound I (where —$X^1$—$R^4$=H).

If the process is carried out in the absence of an inert solvent, an even larger excess may also be expedient.

The reaction temperature is normally from 0° C. to the boiling point of the reaction mixture.

For work-up, the reaction mixture is treated for example with water, whereupon the product can be isolated as usual.

B.3) Halogenation of 4,5-di(trifluoromethyl)pyrazoles I where —$X^1$—$R^4$ is methyl, and reaction of the process products to give other compounds of the formula I:

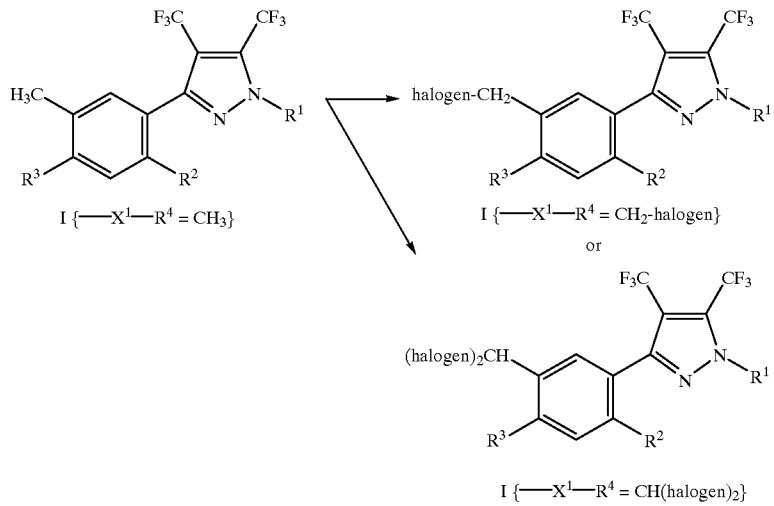

Examples of suitable solvents are organic acids, inorganic acids, aliphatic or aromatic hydrocarbons which can be halogenated, and also ethers, sulfides, sulfoxides and sulfones.

Examples of suitable halogenating agents are chlorine, bromine, N-bromosuccinimides, N-chlorosuccinimides or sulfuryl chloride. Depending on the starting compound and the halogenating agent, the addition of a free-radical initiator, for example an organic peroxide such as dibenzoyl peroxide or an azo compound such as azobisisobutyronitrile, or exposure to light, can have an advantageous effect on the course of the reaction.

The amount of halogenating agent is not critical. Both substoichiometric amounts and large excesses of halogenating agent based on the compound I (where —$X^1$—$R^4$= methyl) to be halogenated are possible.

When using a free-radical initiator, a catalytic amount will normally suffice.

The reaction temperature is normally at from (−100) to 200° C., mostly at from 10 to 100° C. or the boiling point of the reaction mixture.

Those halogenating products I where —$X^1$—$R^4$=—$CH_2$-halo can be converted into their corresponding ethers, thioethers, esters, amines or hydroxylamines in a nucleophilic substitution reaction:

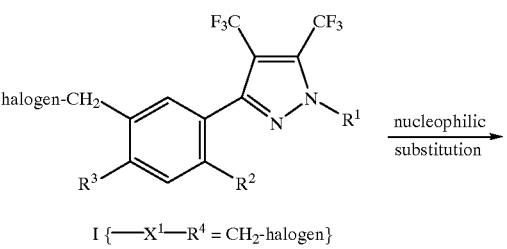

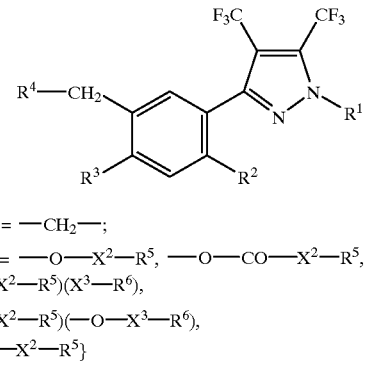

I {$X^1$ = —$CH_2$—;

$R^4$ = —O—$X^2$—$R^5$, —O—CO—$X^2$—$R^5$,

—N($X^2$—$R^5$)($X^3$—$R^6$),

—N($X^2$—$R^5$)(—O—$X^3$—$R^6$),

—S—$X^2$—$R^5$}

The nucleophiles used are either the corresponding alcohols, thiols, carboxylic acids or amines, in which case the process is preferably carried out in the presence of a base (eg. an alkali metal hydroxide or alkaline earth metal hydroxide or an alkali metal carbonate or alkaline earth metal carbonate), or the alkali metal salts of these compounds which have been obtained by reacting the alcohols, thiols, carboxylic acids or amines with a base (eg. an alkali metal hydride) are used.

Suitable solvents are, mainly, aprotic organic solvents, eg. tetrahydrofuran, dimethylformamide, dimethyl sulfoxide, or hydrocarbons such as toluene and n-hexane.

The reaction is carried out at from the melting point to the boiling point of the reaction mixture, preferably at from 0 to 100° C.

Those halogenation products I where $-X^1-R^4=-CH$(halo)$_2$ can be hydrolyzed to give the corresponding aldehydes (I where $-X^1-R^4=CHO$). The latter, in turn, can then be oxidized to give compounds I where $-X^1-R^4=COOH$:

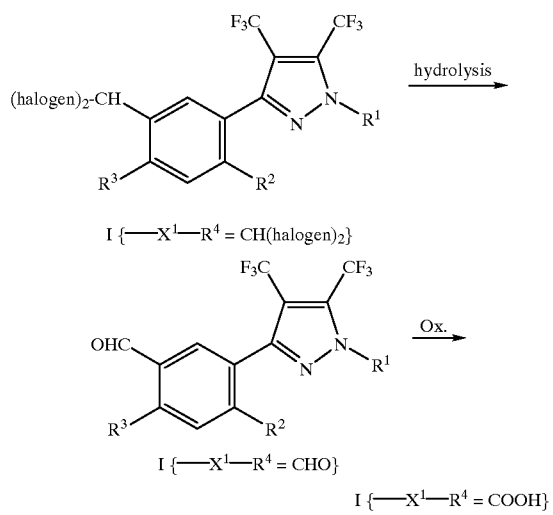

The compounds I where $-X^1-R^4$=dihalomethyl are preferably hydrolyzed under acidic conditions, in particular in the absence of a solvent in hydrochloric acid, acetic acid, formic acid or sulfuric acid, or else in an aqueous solution of one of the abovementioned acids, eg. in a mixture of acetic acid and water (for example 3:1).

The reaction temperature is normally at from 0 to 120° C.

The hydrolysis products I where $-X^1-R^4$=formyl can be oxidized in a manner known per se to give the corresponding carboxylic acids, eg. by the method of Kornblum (see, in this context, in particular pages 179 to 181 of the volume "Methods for the Oxidation of organic Compounds" by A. H. Haines, Academic Press 1988, in the series "Best Synthetic Methods").

An example of a suitable solvent is dimethyl sulfoxide.

The compounds I where $-X^1-R^4$=formyl can also be olefinated in a manner known per se to give compounds I where $X^1$=unsubstituted or substituted ethene-1,2-diyl:

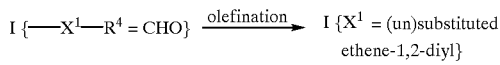

The olefination is preferably carried out by the method of Wittig or one of its modifications, suitable reactants being phosphorylides, phosphonium salts and phosphonates, or by means of aldole condensation.

When using a phosphonium salt or a phosphonate, it is recommended to carry out the process in the presence of a base, especially suitable substances being alkali metal alkyls such as n-butyllithium, alkali metal hydrides and alkali metal alcoholates such as sodium hydride, sodium ethanolate and potassium tert-butanolate, and alkali metal hydroxides and alkaline earth metal hydroxides such as calcium hydroxide.

To achieve a complete reaction, all reactants are employed in an approximately stoichiometric ratio, but it is preferred to employ an excess of phosphorus compound and/or base of up to approximately 10 molt based on the starting compound (I where $-X^1-R^4$=formyl).

The reaction temperature is generally at from (–40) to 150° C.

The 4,5-di(trifluoromethyl)pyrazoles I where $-X^1-R^4$=formyl can be converted in a manner known per se to give compounds I where $-X^1-R^4=-CO-X^2-R^5$, for example by reacting them with a suitable organometal compound Me—$X^2$—$R^5$—where Me is preferably lithium or magnesium—followed by oxidation of the resulting alcohols (cf., for example, J. March, Advanced Organic Chemistry, 3rd ed., John Wiley, New York 1985, p. 816 et seq. and 1057 et seq.).

The compounds I where $-X^1-R^4=-Co-X^2-R^5$, in turn, can be further reacted in a Wittig reaction.

Those phosphonium salts, phosphonates or phosphorylides which are required as reactants and which are not already known can be prepared in a manner known per se {cf., in this context, for example Houben-Weyl, Methoden der Organischen Chemie [Methods in Organic Chemistry], Vol. E1, p. 636 et seq. and Vol. E2, p. 345 et seq., Georg Thieme Verlag Stuttgart 1982; Chem. Ber. 95, 3993 (1962)}.

Other possibilities of synthesizing other 4,5-di (trifluoromethyl)pyrazoles I from compounds I where $-X^1-R^4$=formyl include the aldol condensation, which is known per se, and condensation reactions by the methods of Knoevenagel or Perkin. Suitable conditions for these processes can be found, for example, in Nielson, Org. React. 16, 1 et seq. (1968) {aldol condensation} Org. React. 15 , 204 et seq. (1967) {Knoevenagel condensation} and Johnson, Org. React. 1, 210 et seq. (1942) {Perkin condensation}.

In general, the compounds I where $-X^1-R^4=-CO-X^2-R^5$ can also be converted into their corresponding oximes in a manner known per se {cf., in this context, for example Houben-Weyl, Methoden der Organischen Chemie [Methods in Organic Chemistry], Georg Thieme Verlag Stuttgart, Vol. 10/4, 4th Edition 1968, p. 55 et seq. and p. 73 et seq.}:

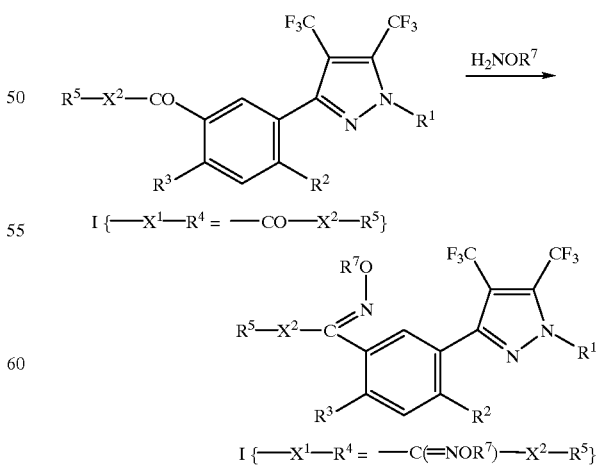

B.4) Synthesis of ethers, thioethers, amines, esters, amides, sulfonamides, thioesters and hydroxamic esters:

4,5-di(trifluoromethyl)pyrazoles I where $R^4$=is hydroxyl, amino, —NH—$X^2$—$R^5$, hydroxylamino, —N($X^2$—$R^5$)—OH, —NH—O—$X^2$—$R^5$, mercapto, halosulfonyl, —C(=NOH)—$X^2$—$R^5$ or carboxyl can be converted in a manner known per se by means of alkylation, acylation, sulfonation, esterification or amidation to give the corresponding ethers {I where $R^4$=—O—$X^2$—$R^5$}, ester {I where $R^4$=—O—CO—$X^2$—$R^5$}, amines {I where $R^4$=—N($X^2$—$R^5$)($X^3$—$R^6$)}, amides {I where $R^5$=N($X^2$—$R^5$)—CO—$X^3$—$R^6$}, sulfonamides {I where $R^4$=N($X^2$—$R^5$)—$SO_2$—$X^3$—$R^6$ or —N ($SO_2$—$X^2$—$R^5$) ($SO_2$—$X^3$—$R^6$) }, hydroxylamines {I where $R^4$=—N($X^2$—$R^5$)(O—$X^3$—$R^6$)}, thioethers {I where $R^4$=—S—$X^2$—$R^5$}, sulfonic acid derivatives {I where $R^4$=—$SO_2$—$X^2$—$R^5$, —$SO_2$—O—$X^2$—$R^5$ or —$SO_2$—N ($X^2$—$R^5$) ($X^3$—$R^6$)}, oximes {I where $R^4$=—C(=NO$R^7$)—$X^2$—$R^5$} or carboxylic acid derivatives {I where $R^4$=—CO—O—$X^2$—$R^5$, —CO—S—$X^2$—$R^5$, —CO—N ($X^2$—$R^5$) ($X^3$—$R^6$), —CO—N($X^2$—$R^5$)(O—$X^3$—$R^6$)}.

Such reactions are described, for example, in Houben-Weyl, Methoden der Organischen Chemie [Methods in Organic Chemistry], Georg Thieme Verlag Stuttgart (Vol. E16d, p. 1241 et seq.; Vol. 6/1a, 4th Edition 1980, p. 262 et seq.; Vol. 8, 4th Edition 1952, p. 471 et seq., 516 et seq., 655 et seq. and p. 686 et seq.; Vol. 6/3, 4th Edition 1965, p. 10 et seq.; Vol. 9, 4th Edition 1955, p. 103 et seq., 227 et seq., 343 et seq., 530 et seq., 659 et seq., 745 et seq. and p. 753 et seq.; Vol. E5, p. 934 et seq., 941 et seq. and p. 1148 et seq.).

Unless otherwise specified, all the above-described processes are expediently carried out under atmospheric pressure or under the inherent pressure of the reaction mixture in question.

The reaction mixtures are generally worked up in a manner known per se. Unless otherwise specified in the above-described processes, the products of interest are obtained for example after diluting the reaction mixture with water by means of filtration, crystallization or solvent extraction, or by removing the solvent, partitioning the residue in a mixture of water and a suitable organic solvent and working up the organic phase to obtain the product.

The substituted 4,5-di(trifluoromethyl)pyrazoles I can be obtained, from their preparation, as isomer mixtures which, if desired, can, however, be separated into the substantially pure isomers by the methods customary for this purpose, such as crystallization or chromatography, also on an optically active adsorbate. Pure optically active isomers can be prepared advantageously from suitable optically active starting materials.

Agriculturally useful salts of the compounds I can be formed by reacting them with a base of the corresponding cation, preferably an alkali metal hydroxide or alkali metal hydride, or by reacting with an acid of the corresponding anion, preferably of hydrochloric acid, hydrobromic acid, sulfuric acid, phosphoric acid or nitric acid.

Salts of I whose metal ion is other than an alkali metal ion, can also be prepared by double decomposition of the corresponding alkali metal salt in the customary manner, and ammonium, phosphonium, sulfonium and sulfoxonium salts by means of ammonia, phosphonium hydroxides, sulfonium hydroxides or sulfoxonium hydroxides.

The compounds I and their agriculturally useful salts, both in the form of isomer mixtures and in the form of the pure isomers, are suitable as herbicides. The herbicidal compositions comprising I control vegetation on uncultivated land very thoroughly, especially at high rates of application. In crops such as wheat, rice, maize, soybeans and cotton, they act against broad-leaved weeds and grass weeds without damaging the crop plants to a considerable extent. This effect is particularly pronounced at low rates of application.

Taking into consideration the versatility of the application methods, the compounds I, or the herbicidal compositions comprising them, can also be employed in a further number of crop plants for eliminating undesirable plants. Suitable crops are, for example, the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Bevea brasiliensis, Hordeum vulgare, Eumulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec.,*Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays*.

In addition, the compounds I can also be used in crops which have been made tolerant to the action of herbicides by means of breeding, including genetic engineering methods.

Furthermore, the substituted 4,5-di(trifluoromethyl) pyrazoles I are also suitable for the desiccation and/or defoliation of plants.

As desiccants, they are particularly suitable for desiccating the aerial parts of crop plants such as potatoes, oilseed rape, sunflowers and soybeans. This allows completely mechanical harvesting of these important crop plants.

Also of economic interest is facilitated harvesting, which is made possible by dehiscence, or reduced adherence, on the tree over a concentrated period of time in the case of citrus fruits, olives or other species and varieties of pomaceous fruit, stone fruit and hard-shelled fruit. The same mechanism, ie. promotion of the formation of abscission tissue between fruit or leaf and shoot of the plants is also essential for well adjustable defoliation of useful plants, in particular cotton.

Moreover, shortening the interval within which the individual cotton plants mature results in improved fibre quality after harvesting.

The compounds I, or the compositions comprising them, can be applied for example in the form of directly sprayable aqueous solutions, powders, suspensions, also highly-concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Suitable inert auxiliaries are essentially: mineral oil fractions of medium to high boiling point such as kerosine and diesel oil, furthermore coal tar oil and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, adhesive, dispersant or emulsifier. However, it is also possible to prepare concentrates composed of active ingredient, wetting agent, adhesive, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredient to solid carriers. Solid carriers are mineral earths such as silicas, silica gels, silicates, talc, kaolin, limestone, lime, chalk, bole, loess, clay, dolomite and diatomaceous earth, calcium sulfate, magnesium sulfate, magnesium oxide, ground synthetic materials, fertilizers such as ammonium sulfate, ammonium phosphate and ammonium nitrate, ureas and products of vegetable origin such as cereal meal, tree bark meal, wood meal and nutshell meal, cellulose powders or other solid carriers.

The concentrations of the active ingredients I in the ready-to-use preparations can be varied within wide ranges. In general, the formulations comprise approximately 0.001 to 98% by weight, preferably 0.01 to 95% by weight. The active ingredients are employed in a purity of from 90% to 100%, preferably 95% to 100% (according to NMR spectrum).

The formulation examples which follow illustrate the preparation of such products:

I. 20 parts by weight of the compound No. Ia.062 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.027 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ia.028 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ia.078 are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. Ib.062 are mixed with 97 parts by weight of finely divided kaolin. This gives a dust which comprises 3% by weight of the active ingredient.

VI. 20 parts by weight of the active ingredient No. Ic.223 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ic.231 is dissolved in a mixture composed of 70 parts by weight of cyclohexanone, 20 parts by weight of ethoxylated isooctylphenol and 10 parts by weight of ethoxylated castor oil. The mixture can subsequently be diluted with water to the desired concentration of active ingredient. A stable emulsion concentrate is obtained.

VIII. 1 part by weight of the compound No. Ic.298 is dissolved in a mixture composed of 80 parts by weight of cyclohexane and 20 parts by weight of Wettol® EM 31 (=nonionic emulsifier based on ethoxylated castor oil; BASF AG). The mixture can be diluted with water to give the desired concentration of active ingredient. A stable emulsion concentrate is obtained.

The active ingredients I or the herbicidal compositions can be applied pre- or post-emergence. If the active ingredients are less well tolerated by certain crop plants, application techniques can be used where the herbicidal compositions are sprayed, with the aid of the spraying apparatus, in such a way that the leaves of the sensitive crop plants come into as little contact as possible, while the active ingredients reach the leaves of undesirable plants which grow underneath, or the naked soil surface (post-directed, lay-by).

Depending on the intended aim, the season, the target plants and the growth stage, the rates of application of active ingredient I are from 0.001 to 3.0, preferably 0.01 to 1.0, kg/ha of active ingredient (a.i.).

To widen the spectrum of action and to achieve synergistic effects, the substituted 4,5-di(trifluoromethyl)pyrazoles I may be mixed, and applied jointly, with a large number of representatives of other groups of herbicidal or growth-regulating active substances. Suitable components for mixtures are, for example, 1,2,4-thiadiazoles, 1,3,4-thiadiazoles, amides, aminophosphoric acid and its derivatives, aminotriazoles, anilides, aryloxy/heteroaryloxy-alkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, together with further crop protection agents in the form of a mixture, for example with pesticides or with agents for controlling phytopathogenic fungi or bacteria. Also of interest is the miscibility with mineral salt solutions which are employed for treating nutrient and trace element deficiencies. Non-phytotoxic oils and oil concentrates may also be added.

Preparation Examples

EXAMPLE 1

3-(4-Chlorophenyl)-1-methyl-4,5-di (trifluoromethyl)-1H-pyrazole (No. Ia.001)
Step 1: 4-Chlorobenzaldehyde (N-methyl)hydrazone 56.2 g (0.4 mol) of 4-chlorobenzaldehyde were added dropwise to a solution of 18.4 g (0.4 mol) of methylhydrazine in 100 ml of ethanol. The mixture was then refluxed for 4 hours. After cooling, the reaction mixture was concentrated. The residue was taken up in methyl tert-butyl ether. The ether phase was finally washed with water, dried over magnesium sulfate and then concentrated. Yield: 97%.

$^1$H NMR (250 MHz, in $CDCl_3$): δ[ppm]=2.92 and 2.95 (2s, together 3H), 5.67 (s,1H), 7.14–7.50 (m,5H).
Step 2: α-Bromo-4-chlorobenzaldehyde methylhydrazone 9.5 g (0.06 mol) of bromine were added dropwise at (−5) to (−7)° C. to a solution of 10 g (0.06 mol) of 4-chlorobenzaldehyde (N-methyl)hydrazone in 50 ml of acetic acid and 20 ml of acetonitrile. After the mixture had been stirred for 3 hours, the product which had precipitated was separated off and washed with a small amount of pentane. Yield: 61%.

$^1$H NMR (270 MHz, in $CDCl_3$): δ[ppm]=3.30 (s,3H), 7.44 (d,2H), 7.90 (s,1H), 7.92 (d,2H).
Step 3: 3-(4-Chlorophenyl)-1-methyl-4,5-di (trifluoromethyl)-1H-pyrazole (No. Ia.001)

5.7 g (41 nmol) of gaseous hexafluoro-2-butyne were passed at below (−50)° C. into a suspension, cooled to (−70)° C., of 9 g (36 mmol) of α-bromo-4-chlorobenzaldehyde methylhydrazone in 100 ml of toluene. The mixture was subsequently heated to (−25)° C., and 8.4 g (83 mmol) of triethylamine were added dropwise at this temperature. After the mixture had been stirred for 2 hours at this temperature and for a further 16 hours at approx. 20° C., it as washed with water, dried over magnesium sulfate and finally concentrated.

Yield: 75%.

EXAMPLE 2

3-(4-Chloro-3-nitrophenyl)-1-methyl-4,5-di (trifluoromethyl)-1H-pyrazole (No. Ia.003)

9 g (27 mmol) of 3-(4-chlorophenyl)-1-methyl-4,5-di (trifluoromethyl)-1H-pyrazole were added at (−40)° C. to 100 ml of concentrated nitric acid, whereupon the mixture was stirred for 2 hours at this temperature. The solution, which was subsequently warmed to 0° C., was treated with ice-water. The product was subsequently extracted with methyl tert-butyl ether. The organic phase was washed with water, dried over magnesium sulfate and concentrated.

Yield: 97%.

EXAMPLE 3

3-(3-Amino-4-chlorophenyl)-1-methyl-4,5-di (trifluoromethyl)-1H-pyrazole (No. Ia.023)

A solution of 10 g (26 mmol) of 3-(4-chloro-3-nitrophenyl)-1-methyl-4,5-di(trifluoromethyl)-1H-pyrazole in 50 ml of methanol was added dropwise to a mixture, heated at reflux temperature, of 4.5 g (80 mmol) of iron powder and 30 ml of glacial acetic acid. After the mixture had been stirred for 3 hours it was poured into 100 ml of water. Then, 100 ml of ethyl acetate were added to the mixture. The solids were subsequently separated off from the mixture and washed with ethyl acetate. The organic phase was separated off from the combined filtrates, washed with water, dried over magnesium sulfate and finally concentrated.

Yield: 94%.

EXAMPLE 4

3-(4-chloro-3-(N-propargyl)aminophenyl)-1-methyl-4,5-di(trifluoromethyl)-1E-pyrazole (No. Ia.179)

1.6 g (12 mmol) of potassium carbonate and 1.4 g (12 mmol) of 3-bromopropyne were added to a solution of 2 g (5.8 mmol) of 3-(3-amino-4-chlorophenyl)-1-methyl-4,5-di (trifluoromethyl)-1H-pyrazole in 20 ml of dimethylformamide, whereupon the mixture was stirred for 7 hours at 65° C. The reaction mixture was subsequently poured into 100 ml of water. The product was then extracted with ethyl acetate. The organic phase was dried over magnesium sulfate and finally concentrated. The crude product was purified by means of preparative MPLC on silica gel (eluent: cyclohexane/ethyl acetate=4:1). Yield: 9%.

EXAMPLE 5

Ethyl 2-chloro-3-(2-chloro-5-(1-methyl-4,5-di (trifluoromethyl)-1H-pyrazol-3-yl)phenylpropionate (No. Ia.062)

7.8 g (78 mnmol) of ethyl acrylate and 0.45 g (3.4 mmol) of copper(II) chloride were added at 0° C. to a solution of 0.4 g (3.9 mmol) of tert-butyl nitrite in 100 ml of acetonitrile. A solution of 0.9 g (9.4 mmol) of 3-(3-amino-4-chlorophenyl)-1-methyl-4,5-di(trifluoromethyl)-1H-pyrazole in 50 ml of acetonitrile was then added dropwise. After the mixture had been stirred for 3 hours, it was concentrated, whereupon the residue was treated with ethyl acetate. The organic phase was then washed with water, dried over magnesium sulfate and finally concentrated. The crude product was purified by means of silica gel chromatography (eluent: cyclohexane/ethyl acetate=10:1).

Yield: 33%.

EXAMPLE 6

3-(4-Chloro-2-fluorophenyl)-1-methyl-4,5-di(trifluoromethyl)-1H-pyrazole (No. Ib.001)

Step 1: 4-Chloro-2-fluorobenzaldehyde (N-methyl)hydrazone 5.5 g (0.12 mol) of methylhydrazine were added to a solution of 19 g (0.12 mol) of 4-chloro-2-fluorobenzaldehyde in 120 ml of ethanol. After 1 hour, the mixture was concentrated, and the residue was subsequently treated with ethyl acetate. The organic phase was washed with water, dried over magnesium sulfate and finally concentrated. Yield: 94%

$^1$H NMR (270 MHz, in $CDCl_3$): δ[ppm]=2.97 and 2.99 (2s, together 3H), 5.70 and 5,90 (2s, together 1H), 7.08 (m,2H), 7.48 and 7.58 (2s, together 1H), 7.73 and 7.77 (2t, together 1H).

Step 2: 4-Chloro-2-fluorobenzoyl bromide (N-methyl)hydrazonide 12.9 g (80 mmol) of bromine were added to a solution, cooled to (−15)° C., of 15 g (80 mmol) of 4-chloro-2-fluorobenzaldehyde (N-methyl)hydrazone in 60 ml of acetic acid, 30 ml of acetonitrile and 30 ml of tetrahydrofuran. After the mixture had been stirred for 1 hour, the solid product which had formed was separated off and washed with a little n-hexane.

Yield: 58%.

$^1$H NMR (270 MHz, in $CDCl_3$): δ[ppm]=3.24 (s,3H), 7.20 (m,2H), 7.57 (t,1H).

Step 3: 3-(4-Chloro-2-fluorophenyl)-1-methyl-4,5-di(trifluoromethyl)-1H-pyrazole (No. Ib.001)

9.1 g (56 mmol) of hexafluoro-2-butyne were passed into a solution, cooled to (−70)° C., of 12 g (45 mmol) of 4-chloro-2-fluorobenzoyl bromide (N-methyl)hydrazonide in 200 ml of toluene. The mixture was then warmed to (−30)° C., and 14 g (138 mmol) of triethylamine were added dropwise to the reaction mixture. The mixture was subsequently stirred until it had come to approx. 20° C. and was then treated with 200 ml of water. After phase separation, the organic phase was separated off, washed with saturated aqueous sodium chloride solution, dried over magnesium sulfate and finally concentrated. Yield: 68%.

EXAMPLE 7

3-(4-Chloro-2-fluoro-5-nitrophenyl)-1-methyl-4,5-di(trifluoromethyl)-1H-pyrazole (No. Ib.003)

10.5 g (30 mmol) of 3-(4-chloro-2-fluorophenyl)-1-methyl-4,5-di(trifluoromethyl)-1H-pyrazole were added, at (−40)° C. to 90 ml of concentrated nitric acid, whereupon the mixture was stirred for 1 hour. Then, the mixture was stirred in 0.8 l of ice-water. The product of value was subsequently extracted with dichloromethane. The organic phase was dried over magnesium sulfate and finally concentrated. Yield: 59%.

EXAMPLE 8

3-(5-Amino-4-chloro-2-fluorophenyl)-1-methyl-4,5-di(trifluoromethyl)-1H-pyrazole (No. Ib.023)

4,6 g (83 mmol) of iron powder, 14 ml of glacial acetic acid and 30 ml of ethanol were heated to 70–75° C. and the mixture was treated with 7 g (17 mmol) of 3-(4-chloro-2-fluoro-5-nitrophenyl)-1-methyl-4,5-di(trifluoromethyl)-1H-pyrazole. After the mixture had been stirred for 2 hours at reflux temperature, it was treated with 100 ml of ethyl acetate. The mixture was then filtered through kieselguhr, whereupon the filtrate was washed with saturated aqueous sodium hydrogen carbonate solution, dried over magnesium sulfate and finally concentrated. The residue was purified by means of silica gel chromatography (eluent: hexane/ethyl acetate=4:1). Yield: 22%.

EXAMPLE 9

3-(4-Chloro-2-fluoro-5-(di(methylsulfonyl))aminophenyl)-1-methyl-4,5-di(trifluoromethyl)-1H-pyrazole (No. lb.027)

1 g (10 mmol) of triethylamine and 0.8 g (6.6 mmol) of methanesulfonyl chloride were added in succession to a solution of 1.2 g (3.3 mmol) of 3-(5-amino-4-chloro-2-fluorophenyl)-1-methyl-4,5-di(trifluoromethyl)-1H-pyrazole in 30 ml of tetrahydrofuran. The reaction mixture was subsequently stirred for 16 hours, whereupon it was concentrated. The residue was treated with water and ethyl acetate. The organic phase which had been separated off was washed with water and saturated aqueous sodium chloride solution, dried over magnesium sulfate and finally concentrated. Yield: quantitative.

EXAMPLE 10

3-(4-Chloro-2-fluoro-5-(methylsulfonyl)aminophenyl)-1-methyl-4,5-di(trifluoromethyl)-1H-pyrazole (No. Ib.028)

0.31 g (4.6 mmol) of potassium hydroxide were added to a solution of 1.2 g (2.3 mmol) of 3-(4-chloro-2-fluoro-5-(di(methyl-sulfonyl))-aminophenyl)-1-methyl-4,5-di(trifluoromethyl)-1H-pyrazole in 100 ml of methanol. The reaction mixture was then stirred for 30 minutes, whereupon it was concentrated. The residue was treated with water and ethyl acetate, whereupon the organic phase was separated off, washed with water and saturated aqueous sodium chloride solution, dried over magnesium sulfate and finally concentrated. The residue was purified by recrystallization from ethyl acetate/hexane. Yield: 59%.

EXAMPLE 11

3-(2,4-Dichlorophenyl)-1-methyl-4,5-di(trifluoromethyl)-1H-pyrazole (No. Ic.001)

Step 1: 2,4-Dichlorobenzaldehyde (N-methyl)hydrazone 263 g (5.7 mol) of methylhydrazine were treated with a solution of 200 g (1.14 mol) of 2,4-dichlorobenzaldehyde in 1.2 l of ethanol. After the mixture had been stirred for 48 hours, the small amount of solids present was filtered off and the filtrate was then concentrated. Yield: quantitative.

$^1$H NMR (250 MHz, in $CDCl_3$): δ[ppm]=2.99 and 3.01 (2s, together 3H), 5.90 (s,1H), 7.18 (dd,1H), 7.32 (d,1H), 7.71 (s,1H), 7.82 (d,1H).

Step 2: 2,4-Dichlorobenzoyl bromide (N-methyl)hydrazonide 16.2 g (0.10 mol) of bromine were added to a solution, cooled to (−15)° C., of 20.5 g (0.10 mol) of 2,4-dichlorobenzaldehyde (N-methyl)hydrazone in 76 ml of acetic acid, 38 ml of acetonitrile and 38 ml of tetrahydrofuran. After the mixture had been stirred for 1 hour, the solid product was separated off and washed with a little hexane. Yield: 88%.

$^1$H NMR (270 MHz, in CDCl$_3$): δ[ppm]=3.29 (s,3H), 7.36 (dd,1H), 7.45 (m,2H), 8.10 (s,1H).

Step 3: 3-(2,4-Dichlorophenyl)-1-methyl-4,5-di(trifluoromethyl)-1H-pyrazole (No. Ic.001)

17.3 g (106 mmol) of hexafluoro-2-butyne were passed into a solution, cooled to (−70)° C., of 25 g (89 mmol) of 2,4-dichlorobenzoyl bromide (N-methyl)hydrazonide in 350 ml of toluene. The mixture was subsequently warmed to (−30)° C., and 27 g (0.27 mol) of triethylamine were added dropwise. The mixture was then stirred until it had come to approx. 20° C., and 350 ml of water were then added. The organic phase was separated off, washed with saturated aqueous sodium chloride solution, dried over magnesium sulfate and finally concentrated. Yield: 70%.

EXAMPLE 12

3-(2,4-Dichloro-5-nitrophenyl)-1-methyl-4,5-di-(trifluoromethyl)-1H-pyrazole (No. Ic.003)

21 g (58 mmol) of 3-(2,4-dichlorophenyl)-1-methyl-4,5-di-(trifluoromethyl)-1H-pyrazole were added, at (−30)° C., to 250 ml of concentrated nitric acid, whereupon the mixture was stirred for 1 hour at (−10)° C. The solution was subsequently stirred into 1.2 l of ice-water. The product was then extracted with dichloromethane. The organic phase was dried over magnesium sulfate and concentrated.

Yield: 50%

EXAMPLE 13

3-(5-Amino-2,4-dichlorophenyl)-1-methyl-4,5-di(trifluoromethyl)-1H-pyrazole (No. Ic.023)

8 g (0.14 mol) of iron powder, 53 ml of glacial acetic acid and 24 ml of ethanol were heated to 70° C. and the mixture was treated with 11.7 g (29 mmol) of 3-(2,4-dichloro-5-nitrophenyl)-1-methyl-4,5-di(trifluoromethyl)-1H-pyrazole. After the mixture had been stirred for 2 hours at reflux temperature, it was treated with 200 ml of ethyl acetate. It was then filtered through kieselguhr. The filtrate was concentrated. Yield: quantitative.

EXAMPLE 14

3-(2,4-Dichloro-5-methylthiophenyl)-1-methyl-4,5-di(trifluoromethyl)-1H-pyrazole (No. Ic.036)

1.5 g (16 mmol) of dimethyl disulfide and 5.3 g (52 mmol) of tert-butyl nitrite were added to a solution of 2 g (5.3 mmol) of 3-(5-amino-2,4-dichlorophenyl)-1-methyl-4,5-di(trifluoromethyl)-1H-pyrazole in 30 ml of dichloromethane. The reaction mixture was subsequently stirred for 16 hours, whereupon it was washed with water and dilute sodium hydroxide solution, dried over magnesium sulfate and finally concentrated. The residue was purified by means of silica gel chromatography (eluent: hexane/ethyl acetate =4:1). Yield: 37%.

EXAMPLE 15

Ethyl 2-chloro-3-(2,4-dichloro-5-(1-methyl-4,5-di(trifluoro-methyl)-1H-pyrazol-3-yl)phenylacrylate (No. Ic.078)

A solution of 2 g (5.3 mmol) of 3-(5-amino-2,4-dichlorophenyl)-1-methyl-4,5-di(trifluoromethyl)-1H-pyrazole in 50 ml of acetonitrile was added dropwise to a solution of 10.9 g (111 nmol) of ethyl propionate, 0.8 g (5.8 mmol) of copper(II) chloride and 0.6 g (5.6 mmol) of tert-butyl nitrite in 50 ml of acetonitrile. After the mixture had been stirred for 16 hours, it was diluted with 200 ml of methyl tert-butyl ether, whereupon it was washed with dilute hydrochloric acid and saturated aqueous sodium chloride solution, dried over magnesium sulfate and finally concentrated. The residue was purified by means of silica gel chromatography (eluent: hexane/ethyl acetate=9:1). Yield: 19%.

In addition to the compounds described above, other substituted 4,5-di(trifluoromethyl)pyrazoles I which were, or can be, prepared in a similar manner are listed in Tables 2 to 4 which follow:

TABLE 2

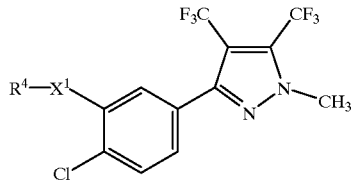

Ia (R$^1$ = CH$_3$, R$^2$ = H, R$^3$ = Cl)

| No. | —X$^1$—R$^4$ | m.p./$^1$H NMR [ppm]/MS [m/z] |
|---|---|---|
| Ia.001 | —H | 4.12 (s, 3H), 7.42 (d, 2H), 7.45 (d, 2H) |
| Ia.003 | —NO$_2$ | 4.15 (s, 3H), 7.63 (d, 1H), 7.68 (d, 1H), 8.10 (s, 1H) |
| Ia.006 | —Cl | 4.12 (s, 3H), 7.34 (d, 1H), 7.52 (d, 1H), 7.64 (d, 1H) |
| Ia.023 | —NH$_2$ | 4.10 (s, 3H), 4.30 (s, 2H), 6.82 (d, 1H), 6.90 (s, 1H), 7.30 (d, 1H) |

TABLE 2-continued

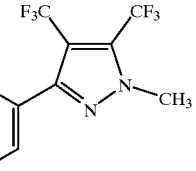

Ia (R¹ = CH₃, R² = H, R³ = Cl)

| No. | —X¹—R⁴ | m.p./¹H NMR [ppm]/MS [m/z] |
|---|---|---|
| Ia.027 | —N(SO₂—CH₃)₂ | 3.50 (s, 6H), 4.13 (s, 3H), 7.48 (s, 1H), 7.62 (s, 2H) |
| Ia.028 | —NH—SO₂—CH₃ | 3.07 (s, 3H), 4.13 (s, 3H), 6.88 (s, 1H), 7.29 (d, 1H), 7.50 (d, 1H), 7.85 (s, 2H) |
| Ia.062 | —CH₂—CH(Cl)—CO—OC₂H₅ | 1.24 (t, 3H), 3.33 (dd, 1H), 3.56 (dd, 1H), 4.11 (s, 3H), 4.20 (m, 2H), 4.60 (t, 1H), 7.26 (s, 1H), 7.37 (d, 1H), 7.44 (d, 1H) |
| Ia.078 | —CH=C(Cl)—CO—OC₂H₅ | 460 [M]⁺, 425 [M-Cl]⁺ |
| Ia.179 | —NH—CH₂—C≡CH | 2.26 (t, 1H), 4.02 (dd, 2H), 4.11 (s, 3H), 4.64 (t, 1H), 6.85 (d, 1H), 6.90 (s, 1H), 7.33 (d, 1H) |

TABLE 3

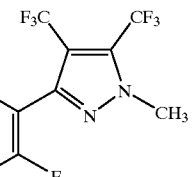

Ib (R¹ = CH₃, R² = F, R³ = Cl)

| No. | —X¹—R⁴ | m.p./¹H NMR [ppm]/MS [m/z] |
|---|---|---|
| Ib.001 | —H | 4.13 (s, 3H), 7.15–7.25 (m, 2H), 7.38 (t, 1H) |
| Ib.003 | —NO₂ | 4.16 (s, 3H), 7.41 (d, 1H), 8.14 (d, 1H) |
| Ib.023 | —NH₂ | 3.98 (s, 2H), 4.12 (s, 3H), 6.80 (d, 1H), 7.11 (d, 1H) |
| Ib.027 | —N(SO₂—CH₃)₂ | 156–158° C. |
| Ib.028 | —NH—SO₂—CH₃ | 106–109° C. |
| Ib.062 | —CH₂CH(Cl)—CO—OC₂H₅ | 1.25 (t, 3H), 3.32 (dd, 1H), 3.50 (dd, 1H), 4.13 (s, 1H), 4.21 (m, 2H), 4.59 (t, 1H), 7.24 (d, 1H), 7.40 (d, 1H) |

TABLE 4

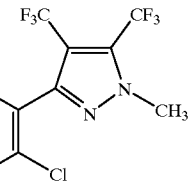

Ic (R¹ = CH₃, R² = R³ = Cl)

| No. | —X¹—R⁴ | m.p./¹H NMR [ppm]/MS [m/z] |
|---|---|---|
| Ic.001 | —H | 4.12 (s, 3H), 7.27 (d, 1H), 7.33 (dd, 1H), 7.50 (d, 1H) |

TABLE 4-continued

Ic ($R^1$ = $CH_3$, $R^2$ = $R^3$ = Cl)

| No. | —$X^1$—$R^4$ | m.p./$^1$H NMR [ppm]/MS [m/z] |
|---|---|---|
| Ic.003 | —$NO_2$ | 4.15 (s, 3H), 7.82 (s, 1H), 7.97 (s, 1H) |
| Ic.023 | —$NH_2$ | 4.13 (s, 5H), 6.74 (s, 1H), 7.38 (s, 1H) |
| Ic.026 | —NH—CO—$CH_3$ | 2.24 (s, 3H), 4.12 (s, 3H), 7.50 (s, 1H), 7.60 (s, 1H), 8.53 (s, 1H) |
| Ic.027 | —N($SO_2$—$CH_3$)$_2$ | 3.48 (s, 6H), 4.15 (s, 3H), 7.41 (s, 1H), 7.70 (s, 1H) |
| Ic.036 | —$SCH_3$ | 2.47 (s, 3H), 4.13 (s, 3H), 7.08 (s, 1H), 7.48 (s, 1H) |
| Ic.038 | —SO—$CH_3$ | 119–122° C. |
| Ic.039 | —$SO_2$—$CH_3$ | 200° C. |
| Ic.042 | —SO—$NH_2$ | 178–180° C. |
| Ic.043 | —$SO_2$—NH—$CH_3$ | 139–141° C. |
| Ic.044 | —$SO_2$—N($CH_3$)$_2$ | 155–157° C. |
| Ic.062 | —$CH_2$—CH(Cl)—CO—$OC_2H_5$ | 1.18 (t, 3H), 3.34 (dd, 1H), 3.52 (dd, 1H), 4.17 (q, 2H), 4.19 (s, 3H), 4.90 (t, 1H) 7.58 (s, 1H), 7.85 (s, 1H) |
| Ic.078 | —CH=C(Cl)—CO—$OC_2H_5$ | 1.11 and 1.39 (2t, together 3H), 4.12 and 4.38 (2m, together 5H), 7.26 and 7.27 (2s, together 1H), 7.55 and 7.60 (2s, together 1H), 7.99 and 8.10 (2s, together 1H) |
| Ic.223 | —$SCH_2$C≡CH | 74–80° C. |
| Ic.231 | —$SCH_2$—CO—$OCH_3$ | 104–106° C. |
| Ic.298 | —$SO_2$—N($CH_3$)—$CH_2$—CO—$OCH_3$ | 100–102° C. |
| Ic.299 | —$SO_2$—N($CH_3$)—$CH_2$—CO—$OC_2H_5$ | 97–99° C. |
| Ic.587 | —$SO_2$—[2-($COOCH_3$)-pyrrolidin-1-yl] | 553 [M]$^+$, 494 [M-$COOCH_3$]$^+$ |

Use Examples (Herbicidal Activity)

The herbicidal action of the substituted 4,5-di(trifluoromethyl)pyrazoles I was demonstrated by the following greenhouse experiments:

The culture containers used were plastic flowerpots containing loamy soil with approximately 3.0% of humus as the substrate. The seeds of the test plants were sown separately for each species.

In the pre-emergence treatment, the active ingredients which had been suspended or emulsified in water were applied immediately after sowing by means of finely distributing nozzles. The containers were irrigated gently to promote germination and growth and subsequently covered with translucent plastic hoods until the plants had rooted. This cover causes uniform germination of the test plants, unless this has been adversely affected by the active ingredients.

For the post-emergence treatment, the test plants were first grown to a plant height of 3 to 15 cm, depending on the growth habit, and only then treated with the active ingredients which had been suspended or emulsified in water. The test plants were either sown directly and grown in the same containers or first grown separately as seedlings and transplanted into the test containers a few days prior to treatment. The rate of application for post-emergence treatment was 0.5 kg/ha of a.i. (active ingredient).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

The plants used in the greenhouse experiments belonged to the following species:

| Scientific name | Common name |
|---|---|
| Centaurus cyanus | cornflower |
| Galium aparine | catchweed bedstraw |
| Ipomoea subspecies | morningglory |
| Viola arvensis | violet |

The compound No. Ia.062 applied post-emergence at a rate of 0.5 kg/ha of a.i. has a very good herbicidal against the abovementioned broad-leaved plants.

Use Examples (Desiccant/Defoliant Activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to drip point using aqueous preparations of the active ingredients (with an addition of 0.15% by weight of the fatty alcohol alkoxylate Plurafac LF 700, based on the spray mixture). The amount of water applied was 1000 l/ha (converted). After 13 days, the number of shed leaves and the degree of defoliation in % were determined.

No leaf drop was observed in the untreated control plants.

We claim:

1. A substituted 4,5-di(trifluoromethyl)pyrazole of the formula I

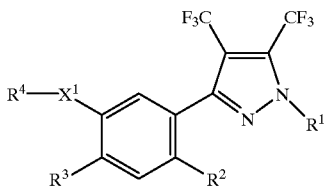

where the variables have the following meanings:

$R^1$ is $C_1$–$C_4$-alkyl or $C_1$–$C_4$-haloalkyl;

$R^2$ is hydrogen;

$R^3$ is cyano, halogen, $C_1$–$C_4$-alkyl or $C_1$–$C_4$-haloalkyl;

$R^4$ is hydrogen, nitro, halogen, —N($X^2$—$R^5$)($X^3$—$R^6$), —N($X^2$—$R^5$)—$SO_2$—$X^3$—$R^6$, —N($SO_2X^2$—$R^5$)($SO_2$—$X^3$—$R^6$), —N($X^2$—$R^5$)(CO—$X^3$—$R^6$), —S—$X^2$—$R^5$, —SO—$X^2$—$R^5$, —$SO_2$—$X^2$—$R^5$, —$SO_2$—O—$X^2$—$R^5$, —$SO_2$—N($X^2$—$R^5$)($X^3$—$R^6$), —CO—$X^2$—$R^5$, —CO—O—$X^2R^5$, CO—N($X^2$—$R^5$)(($X^3$—$R^6$);

$X^1$ is —$CH_2$CH(halo)— or —CH=C(halo)—;

$X^2$ and $X^3$ independently of one another are a chemical bond or an ethene-1,2-diyl, methylene, ethylene or propane-1,3-diyl chain, each of which may be unsubstituted or have attached to it one or two of the following substituents: halogen, cyano, carboxyl, $C_1$–$C_4$-alkyl, $C_1$–$C_4$-haloalkyl, ($C_1$–$C_4$-alkoxy) carbonyl, $C_1$–$C_4$-alkoxy, di-($C_1$–$C_4$-alkyl)amino, $C_1$–$C_6$-haloalkyl and/or phenyl, which, in turn, may have attached to it one to three halogen atoms, nitro, carboxyl, $C_1$–$C_4$-alkyl, $C_1$–$C_4$-haloalkyl and/or ($C_1$–$C_4$-alkoxy)carbonyl groups, the methylene, ethylene or propane-1,3-diyl chain optionally having attached to it a hydroxyl, amino or $C_1$–$C_4$-alkylamino radical;

$R^5$ and $R^6$ independently of one another are —Z—$R^8$, hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalky which may contain a carbonyl or thiocarbonyl ring member, phenyl or 3- to 7-membered heterocyclyl which may contain a carbonyl or thiocarbonyl ring member, the cycloalkyl rings, the phenyl ring and the heterocyclyl rings optionally being unsubstituted or having attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-(alkoxy)carbonyl, ($C_1$–$C_4$-haloalkyl)carbonyl, ($C_1$–$C_4$-alkyl)carbonyloxy, ($C_1$–$C_4$-haloalkyl)carbonyloxy and di-($C_1$–$C_4$-alkyl)amino;

$R^7$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$cycloalkyl, phenyl or phenyl-$C_1$–$C_4$-alkyl;

Z is methylene which may be unsubstituted or have attached to it one or two substituents, in each case selected from the group consisting of $C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_4$-alkoxy)carbonyl-$C_1$–$C_4$-alkyl and phenyl-$C_1$–$C_4$-alkyl, the phenyl ring optionally being unsubstituted or having attached to it, in turn, one to three radicals, in each case selected from the group consisting of halogen, cyano, nitro, carboxyl, $C_1$–$C_4$-alkyl, $C_1$–$C_4$-haloalkyl and ($C_1$-$C_4$-alkoxy)carbonyl;

$R^8$ is hydrogen, nitro, cyano, halogen, —$OR^9$, —N($R^9$)$R^{10}$, —N($R^9$)—$OR^{10}$, —$SR^9$, —SO—$R^9$, —$SO_2$—$R^9$, —$SO_2$—$OR^9$, —$SO_2$—N($R^9$)$R^{10}$, —CO—$R^9$, —C(=$NOR^{11}$)—$R^9$, —CO—$OR^9$, —CO—$SR^9$, —CO—N($R^9$)$R^{10}$ or —CO—N($R^9$)—$OR^{10}$;

$R^9$ and $R^{10}$ independently of one another are hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, the cycloalkyl and heterocyclyl rings optionally containing in each case one carbonyl or thiocarbonyl ring member and the cycloalkyl, phenyl and heterocyclyl rings optionally being unsubstituted or having attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl)carbonyloxy and di-($C_1$–$C_4$-alkyl)amino;

$R^{11}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl-$C_1$–$C_4$-alkyl;

or an agriculturally useful salt of compound I.

2. Substituted 4,5-di(trifluoromethyl)pyrazoles of the formula I and their agriculturally useful salts as claimed in claim 1, for use as herbicides or for the desiccation/defoliation of plants, wherein $R^4$ is —CO—O—$X^2$—$R^5$ or —$CO_2$—N($X^2$—$R^5$)($X^3$—$R^6$), and $X^1$ is —$CH_2$CH(halo)— or —CH=C(halo)—.

3. A herbicidal composition comprising a herbicidally effective amount of at least one substituted 4,5-di (trifluoromethyl)-pyrazole of the formula I or of an agriculturally useful salt of formula I, as claimed in claim 2 and at least one inert liquid and/or solid carrier and, optionally, at least one surfactant.

4. A composition for the desiccation and/or defoliation of plants, comprising such an amount of at least one substituted 4,5-di(trifluoromethyl)pyrazole of the formula I or of an agriculturally useful salt of formula I, as claimed in claim 2 that it acts as a desiccant and/or defoliant, and at least one inert liquid and/or solid carrier and, optionally, at least one surfactant.

5. A process for the preparation of herbicidally active compositions, which comprises mixing a herbicidally active amount of at least one substituted 4,5-di(trifluoromethyl)-pyrazole of the formula I or of an agriculturally useful salt of formula I, as claimed in claim 2 and at least one inert liquid and/or solid carrier and, optionally, at least one surfactant.

6. A process for the preparation of compositions which have a desiccant and/or defoliant action, which comprises mixing such an amount of at least one substituted 4,5-di (trifluoromethyl)pyrazole of the formula I or of an agriculturally useful salt of formula I, as claimed in claim 2 that it acts as a desiccant and/or defoliant and at least one inert liquid and/or solid carrier and, optionally, at least one surfactant.

7. A method of controlling undesirable vegetation, which comprises applying a herbicidally active amount of at least one substituted 4,5-di(trifluoromethyl)pyrazole of the formula I or of an agriculturally useful salt of formula I, as claimed in claim 2 to plants, their environment or on seed.

8. A method for the desiccation and/or defoliation of plants, which comprises applying such an amount of at least one substituted 4,5-di(trifluoromethyl)pyrazole of the formula I or of an agriculturally useful salt of formula I, as claimed in claim 2 to plants that it acts as a desiccant and/or defoliant.

9. A process as claimed in claim 8, wherein the plants are cotton plants.

10. A process for the preparation of a substituted 4,5-di (trifluoromethyl)pyrazole of the formula I, as claimed in claim 1, wherein an acid halide hydrazonide III

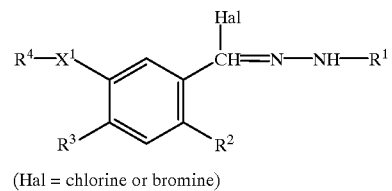

(Hal = chlorine or bromine)

or an acid addition salt thereof is reacted, in the presence of a base, with hexafluoro-2-butyne or with a hexafluorobutene derivative of the formula IV

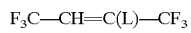    IV, where L is a customary leaving group.

* * * * *

UNITED STATES PATENT AND TRADEMARK OFFICE
CERTIFICATE OF CORRECTION

PATENT NO.: 6,054,412

DATED: April 25, 2000

INVENTOR(S): ZAGAR et al.

It is certified that error appears in the above-identified patent and that said Letters Patent is hereby corrected as shown below:

Title Page, line 25, the correct PCT Publication number is WO97/15559, not WO97/15509.

Column 49, claim 8, line 14, after "plants" insert --so--.

Signed and Sealed this

Twentieth Day of March, 2001

Attest:

NICHOLAS P. GODICI

Attesting Officer     Acting Director of the United States Patent and Trademark Office